US 7,130,459 B2

(12) United States Patent
Anderson et al.

(10) Patent No.: US 7,130,459 B2
(45) Date of Patent: Oct. 31, 2006

(54) REFERENCE DATABASE

(75) Inventors: Norman G. Anderson, Rockville, MD (US); N. Leigh Anderson, Washington, DC (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

(21) Appl. No.: 10/295,840

(22) Filed: Nov. 18, 2002

(65) Prior Publication Data
US 2003/0059095 A1 Mar. 27, 2003

Related U.S. Application Data

(63) Continuation of application No. 09/654,133, filed on Sep. 1, 2000, now Pat. No. 6,539,102.

(51) Int. Cl.
G06K 9/00 (2006.01)
G01N 33/00 (2006.01)
G01N 33/48 (2006.01)

(52) U.S. Cl. .............................. 382/128; 436/86; 702/20
(58) Field of Classification Search ................ 382/128, 382/129, 133; 435/6; 204/459, 461; 702/19, 702/20, 21, 22, 23; 707/104.1; 436/86, 436/89
See application file for complete search history.

(56) References Cited
U.S. PATENT DOCUMENTS

| | | | |
|---|---|---|---|
| 4,031,201 A | 6/1977 | Lostia et al. | |
| 4,289,623 A | 9/1981 | Lee | |
| 4,938,591 A | 7/1990 | Anderson et al. | |
| 5,073,495 A | 12/1991 | Anderson | |
| 5,073,963 A | 12/1991 | Sammons et al. | |
| 5,169,720 A | 12/1992 | Braatz et al. | |
| 5,186,824 A | 2/1993 | Anderson et al. | |
| 5,187,763 A | 2/1993 | Tu | |
| 5,193,056 A | 3/1993 | Boes | |
| 5,270,193 A | 12/1993 | Eveleigh | |
| 5,272,075 A | 12/1993 | Anderson et al. | |
| 5,273,656 A | 12/1993 | Anderson et al. | |
| 5,434,049 A | 7/1995 | Okano et al. | |
| 5,498,530 A | 3/1996 | Schatz et al. | |
| 5,506,117 A | 4/1996 | Andrews et al. | |
| 5,538,897 A * | 7/1996 | Yates et al. ................ 436/89 |
| 5,545,531 A | 8/1996 | Rava et al. | |
| 5,635,597 A | 6/1997 | Barrett et al. | |
| 5,723,286 A | 3/1998 | Dower et al. | |
| 5,763,175 A | 6/1998 | Brenner | |
| 5,780,272 A | 7/1998 | Jarrell | |
| 5,800,268 A | 9/1998 | Molnick | |
| 5,800,992 A | 9/1998 | Fodor et al. | |
| 5,830,677 A | 11/1998 | Wu et al. | |

(Continued)

FOREIGN PATENT DOCUMENTS

WO   WO 99/27105   6/1999

(Continued)

OTHER PUBLICATIONS

Anderson, et al., "Back to the Future: The Human Protein Index and the Agenda for Post-Proteomic Biology", *Proteomics* (2001) 1(1):1-15.

(Continued)

*Primary Examiner*—Vikkram Bali
(74) *Attorney, Agent, or Firm*—John Robbins; John Tarcza; Thomas Gallegos

(57) ABSTRACT

Data acquisition and cataloging are used to classify polypeptides into a reference index or database. The database can be used to identify previously unidentified samples. New polypeptides are characterized and added to the database.

18 Claims, 6 Drawing Sheets

U.S. PATENT DOCUMENTS

| | | | |
|---|---|---|---|
| 5,837,196 | A | 11/1998 | Pinkel et al. |
| 5,843,767 | A | 12/1998 | Beattie |
| 5,885,837 | A | 3/1999 | Winkler et al. |
| 5,953,727 | A * | 9/1999 | Maslyn et al. .......... 707/104.1 |
| 5,961,923 | A | 10/1999 | Nova et al. |
| 5,993,627 | A | 11/1999 | Anderson et al. |
| 5,993,808 | A | 11/1999 | Melchers et al. |
| 6,017,496 | A | 1/2000 | Nova et al. |
| 6,023,659 | A | 2/2000 | Seilhamer et al. |
| 6,027,905 | A | 2/2000 | Keesee et al. |
| 6,029,141 | A | 2/2000 | Bezos et al. |
| 6,035,423 | A | 3/2000 | Hodges et al. |
| 6,051,380 | A | 4/2000 | Sosnowski et al. |
| 6,057,100 | A | 5/2000 | Heyneker |
| 6,110,684 | A | 8/2000 | Kemper et al. |
| 6,146,863 | A | 11/2000 | Palmer et al. |
| 6,188,783 | B1 | 2/2001 | Balaban et al. |
| 6,232,095 | B1 | 5/2001 | Kmiec et al. |
| 6,280,935 | B1 | 8/2001 | Macevicz |
| 6,357,285 | B1 | 3/2002 | Allen |
| 6,539,102 | B1 * | 3/2003 | Anderson et al. .......... 382/128 |
| 6,581,011 | B1 | 6/2003 | Johnson et al. |
| 6,675,104 | B1 | 1/2004 | Paulse et al. |
| 6,692,916 | B1 | 2/2004 | Bevilacqua et al. |
| 2002/0046198 | A1 | 4/2002 | Hitt |
| 2003/0004402 | A1 | 1/2003 | Hitt et al. |
| 2004/0053333 | A1 | 3/2004 | Hitt et al. |
| 2004/0058372 | A1 | 3/2004 | Hitt et al. |
| 2004/0058388 | A1 | 3/2004 | Hitt et al. |

FOREIGN PATENT DOCUMENTS

| | | |
|---|---|---|
| WO | WO 99/28475 | 6/1999 |
| WO | WO 99/44062 | 9/1999 |
| WO | WO 99/46047 | 9/1999 |
| WO | WO 99/51773 | 10/1999 |
| WO | WO 99/60156 | 11/1999 |
| WO | WO 00/00632 | 1/2000 |
| WO | WO 00/04372 | 1/2000 |
| WO | WO 00/09464 | 2/2000 |
| WO | WO 02/056048 | 7/2002 |

OTHER PUBLICATIONS

Anderson, et al., "Twenty years of two-dimensional electrophoresis: past, present and future", *Electrophoresis* (1996) 17:443-453.

Anderson, et al., "A comparison of selected mRNA and protein abundances in human liver", *Electrophoresis* (1997) 18:533-537.

Anderson, et al., "Proteome and Proteomics: New Technologies, new concepts, and new words", *Electrophoresis* (1998) 19:1853-1861.

Anderson, et al., "Some perspectives on two-dimensional protein mapping", *Clin. Chem.* (1984) 30(12):1898-1905.

Anderson, et al., "Towards a complete catalog of human proteins", *Trends in Analytical Chemistry* (1982) 1(6):131-135.

Anderson, et al., "The TYCHO system for computer analysis of 2-D gel electrophoresis patterns", *Clin. Chem.* (1981) 27(11):1807-1820.

Anderson, et al., "The Human Protein Index", *Clin. Chem.* (1982) 28(4):739-748.

Anderson, et al., "The Human Protein Index project and the molecular pathology database", *Med. Laboratory* (1982) 11:75-94.

Anderson, et al., "The Human Protein Index: a prospect for laboratory medicine", *Laboratory Management* (1982) 4:25-32.

Anderson, et al., "Proteins of human urine. I. Concentration & analysis by 2-D electrophoresis", *Clin. Chem.* (1979) 25(7):1199-1210.

Anderson, et al., "Automatic Chemistry and the Human Protein Index", *J. Auto. Chem.* (1980) 2(4):177-178.

Anderson, et al., "Photo Essay / The Human Protein Index", *JAMA*, (1981) 24:2620-21.

Anderson, et al., *Report of the Human Protein Index Task Force* (1980), pp. 1-12, USGPO, Washington, DC.

Anderson, et al., "Analytical techniques for cell fractions. XXI. 2-D analysis of serum & tissue proteins: Multiple isoelectric focusing", *Anal. Biochem.* (1978) 85:331-340.

Giometti, et al., "Mouse liver protein database: A catalog of proteins detected by 2-D gel electrophoresis", *Electrophoresis* (1992) 13:970-991.

Lemkin, "Comparing two-dimensional electrophoretic gels images across the internet", From Genome to Proteome: $2^{nd}$ Siena, Italy 2D Electrophoresis Meeting, Sep. 15-18, 1996 (revised Nov. 20, 1998).

Myers, et al., "A protein expression database for the molecular pharmacology of cancer", *Electrophoresis* (1997) 18:647-653.

Petricoin III, et al., "Use of proteomic patterns is serum to identify ovarian cancer", *Lancet* (2002) 359:572-77.

Taylor, et al., "A computerized system for matching and stretching two-dimensional gel patterns represented by parameter lists", *Electrophoresis* (1981) pp. 383-400.

Taylor, et al., "Numerical measures of 2-D gel resolution & positional reproducibility", *Electrophoresis* (1983) 4:338-346.

Taylor, et al., "Design and implementation of a prototype human protein index", *Clin. Chem.* (1982) 28(4):861-866.

* cited by examiner

REFERENCE DATABASE

This application claims benefit to the filing date of and is a continuation of U.S. Ser. No. 09/654,133, filed Sep. 1, 2000, now U.S. Pat. No. 6,539,102, issued Mar. 25, 2003.

FIELD OF THE INVENTION

The invention relates to methods and means for obtaining, storing and using an index or catalog of proteins. The catalog can be specific for, for example, an organelle, cell, tissue, organ, organism or population.

BACKGROUND OF THE INVENTION

Proteins are the working parts of living cells. With the near completion of the Human Genome Project there is now a need for an integrated system and program for obtaining, organizing, searching, and for using experimentally global information on the protein composition of cells, and on how that composition varies in development, disease, in response to drugs, toxic agents, and other experimental variables.

The human genome is estimated to code for up to 100,000 different proteins. Most if not all are post-translationally modified, and/or are transported from the site of synthesis to the site of function. Many are elements of signaling or communication pathways. The protein composition of cells changes in an organized manner during development, and many cell-specific proteins are known.

Methods for separating or identifying proteins by immunochemical means are widely used and well understood. However, no large-scale systematic means for producing protein-specific antibodies has been described, hence a library of antibodies to match the ever increasing number of isolated proteins or the genomic data from the Human Genome Project does not exist.

The final proof that a given protein is present in a given cell type, and in a specific organelle of that cell type can be provided by immunochemical studies on carefully prepared cell and tissue sections. Many instances of such studies have been reported, however, systematic use of such procedures to confirm the localization of multiple numbers, much less large numbers of proteins has not been described. Such studies cannot proceed in the absence of a library of well-characterized antibodies to a library of specific proteins.

While many of the elements of the multi-dimensional Human Genome Project now exist, at least in part, the extension of that information to systematic large-scale studies requires innovation, automation and integration. Tissue and protein samples and fractions rapidly degrade; hence, it is not feasible to organize a project aimed at characterizing all of the proteins in a fashion similar to the Human Genome Project based on cooperative efforts at many sites. To further handle perishable samples, automation is best developed in intimate contact with an existing operating system. In addition, the elements of an integrated system must match each other in throughput and in time requirements. For example, cell fractionation of sets of tissues obtained at the same time must match the requirements of the next step in the fractionation process. Thus, the hierarchical disassembly of a freshly obtained tissue to cells, subcellular fractions, separation and analysis at the protein level, and data acquisition and analysis must match and must include quality control elements so that key steps may be repeated while the samples are still in good condition and available.

To organize, search and experimentally manipulate information relating to such a large number of functional entities will require both a theoretical framework in which new knowledge can be organized, means for obtaining the wide range of data required, and means for doing the experimental studies required to test new hypothesis. Such means did not exist previously in an integrated or integratable form.

The human body is composed of approximately 252 different cell types, all descendant through different intermediate cells from the three germ layers, and ultimately from a single fertilized human egg. While all diploid cells contain the same genetic information, different genes are expressed in different cell types and at different times during development and during the cell cycle. A protein gene product expressed in several cell types may differ in abundance. In addition, most, if not all proteins are post translationally modified. Further, proteins are synthesized in one set of structures (ribosomes), but target themselves into other subcellular structures.

Proteins are the working parts of living cells. All are parts of self-assembling machines, all can change in abundance in response to experimental and physiological variables, and all turn over constantly, but at different rates. Under starvation conditions the total cell mass may decrease without loss of any individual function of the resting state, and will regain but not exceed a predetermined mass when returned to conditions of normal nutrition, suggesting that the proteome, with its tens of thousands of proteins, is a highly coordinated system.

While collections of proteins are well known, they have not been previously integrated into a unified system able to acquire, organize and sort the data now required to understand both the molecular anatomy and the molecular physiology of man in terms of the human proteome. It is evident that such a system would make possible the detailed description of diseased states, contribute to understanding aging, redefine cancer, and allow both pharmacology and toxicology to be rewritten.

There is therefore an evident need for a cataloging of all of the known proteins that can serve both the passive anatomical function of a data repository and an active physiological function as a search engine for new data and discoveries. An essential attribute of an index is searchability. There is a need for a system, a means and organization to create an index that provides the means for searching the data contained therein for new information and relationships.

It is evident that although some of the data required for such an active index can be acquired from the scientific literature, only an integrated program, analogous to those in atomic physics and space research, can provide and manage the vast amounts of data that can and should be acquired.

A Human Protein Index was hypothesized, Anderson & Anderson, Journal of Automatic Chemistry 2(4):177–178 (1980) and Anderson & Anderson, Clinical Chemistry 28(4): 739–748 (1982), and in conjunction with the human genome project, Anderson & Anderson, American Biotechnology Laboratory September/October 1985. However, heretofore, the materials and methods to allow for the development of such a resource of information were not available.

SUMMARY OF THE INVENTION

The instant invention relates to a method and means for systematically studying proteins to provide data thereon to enable making a catalog of proteins. The method of interest accounts for intertissue and interindividual variability. The method of interest enables the rapid provisional identification of proteins between and among samples. That provisional identification, which later can be confirmed, then can be relied on to develop further provisional identifications of other proteins in the same or other samples. The method reveals sample-specific markers, such as tissue-specific markers. The method provides a protein reference standard be it for an individual protein, a set of proteins or a pattern of polypeptide spots appearing on a 2-D gel. That sort of reference standard can be applied across organelles, tissues, organs, individuals and so on. The catalog of proteins thus is useful for identifying and comparing similar and identical proteins from other sources, such as, other tissues, other individuals of a population and species. The catalog and patterns will reveal relationships between and among proteins, for example, expression thereon under defined conditions, coregulation of proteins and so on. Therefore, proteins that are coordinately expressed or regulated will be revealed, as will proteins with a reciprocal or antagonistic pattern of expression wherein expression of one protein wanes or does not occur when another is expressed. The method yields a reference point for determining the reaction of an individual or a cell, and the proteins thereof, to a stimulus. The method provides a reference point to distinguish manifestations arising from an abnormal state, such as in a disease state. The catalog of proteins is useful for identifying sequences of nucleotides, or clones from a genomic or cDNA bank, that could or do encode a particular protein. As to clones from a genomic bank, knowing the protein will enable determination of what processing of the genomic sequence occurs to obtain expression of the open reading frame. The protein index or database can be aligned, for example, with a chromosomal map or to a morbid gene map to reveal associations with a particular protein and with a particular disease, respectively. Identification of such markers will lend to the development of particular diagnostic and therapeutic materials and methods.

DETAILED DESCRIPTION OF THE INVENTION

Figure 1:
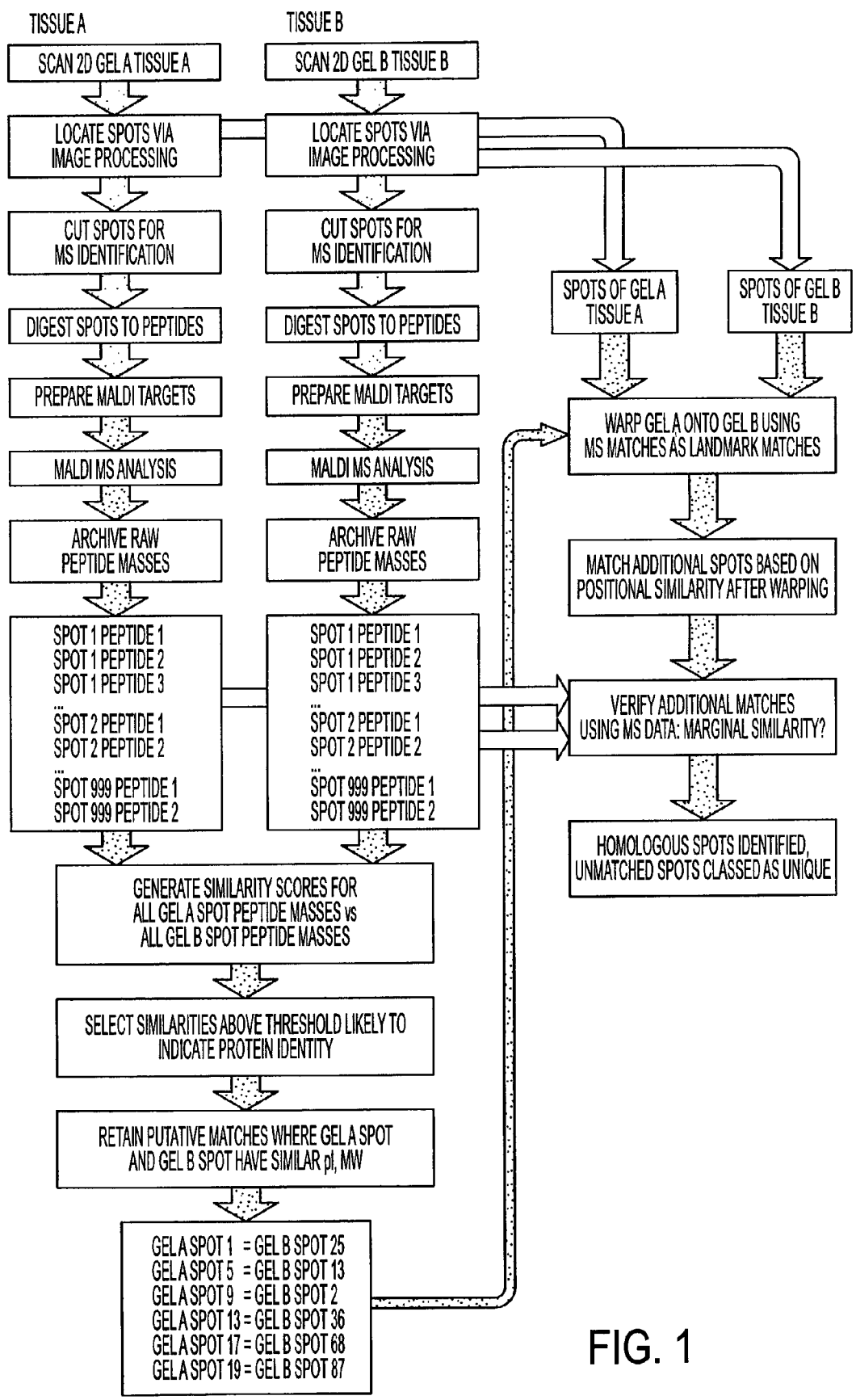
FIG. 1 is a schematic block diagram showing various steps that form part of the analysis for comparing proteins of a plurality of different tissues, each tissue taken from a single species. 2D is two dimensional gel electrophoresis. MALDI is matrix assisted laser desorption/ionization, a form of mass spectrometry (MS). The dark gray arrows depict physical processes, the light gray arrow depict data comparing processes and the black arrows depict data handling processes.

For the purposes of the instant application, a polypeptide or a peptide is a polymer of amino acid monomers of any length, that is, two or more amino acid residues, that is biologically relevant. A protein also is a polymer of amino acid monomers of any length, that is, two or more amino acid residues in length, and which is biologically relevant. Hence, for the purposes of the instant application, the words polypeptide, peptide and protein are used interchangeably. Another synonym is "spot" which in the context of the instant invention, relates to a polypeptide, peptide or protein displayed on a 2-D gel by a particular staining method.

Also for the purposes of the instant application, the assemblage of proteins and the characterizing properties, parameters and features thereof are organized into an index, a listing, a database, a dictionary, a catalog and so on. The result is an ordered set of elements, an element being, for example, a protein and the various distinguishing properties or parameters thereof. The identity of the protein need not be known. All of those terms describe a list of elements that are included into a single assemblage, wherein the elements are characterized by a plurality of features, wherein any one feature can serve as the basis for ordering the elements in the list. Possible features include, total molecular weight, isoelectric point, tissue distribution, molecular weight(s) of specific fragments and so on. For the purposes of the instant application, all of the above terms, and any other used to describe the list of polypeptides or proteins of the instant invention, are used interchangeably.

The protein index or catalog can be obtained for any species or could be an assemblage of proteins from plural species. Preferably, genetically identical individuals or clones are used to avoid normal variation and polymorphisms in a population. Thus, an inbred strain or a clone can be used. However, to obtain an index that is useful at the populational level or that can be used for any wild-type individual from a panmictic population, a number of individuals, inbred strains or clones from different parentals should be investigated to ascertain the level of populational variation.

However, genetically pure populations are not always available, particularly in sexually breeding plants and animals. The problem may be most pronounced in humans and wildlife. In those situations, it is necessary to sample several individuals of a population to determine the level of variation and to deduce an "average" for an individual protein that accounts for the normal variation found in the population.

At another level, it is beneficial to determine the intraindividual level of variation. A reasonable level of comparison would be to compare the proteins from the plural tissues of an individual. Such a comparison would identify those proteins that are similar, those that are identical and those that are specific to, between and among tissues. By monitoring proteins from various tissues, it will be possible to ascertain those proteins that are not altogether identical in physical characteristics, however, carry out the same function.

The term "tissue" is broad and may include different developmental stages of an organ or structure. Particularly in embryos, organ precursor tissue may not have the same function and may comprise numerous different proteins.

Some embryo proteins are never seen again in the adult organism other than perhaps in cancerous tissue. Thus, different developmental stages of the same structure are considered different "tissues".

A preferred approach to control for populational variation of a protein is to sample various tissues of a single individual. That exercise provides information on the normal variation of a protein in an individual, for example, due to post-translational variation, such as variable glycosylation, as well as limited expression in one or more tissues. Thus, at least one tissue is studied from an individual, but preferably, more than one tissue is examined. Therefore, at least 5; at least 6; at least 7; at least 8; at least 9; at least 10; at least 11; at least 12; at least 13; at least 14; at least 15; at least 16; at least 17; at least 18; at least 19; or at least 20 tissues can be studied. More than 20 tissues can be examined, such as 30, 40, 50, 60, 70, 80 or more tissues, and at some point in time, all tissues of an individual will be studied to ascertain the various classes of proteins, such as the intertissue distribution of a protein, tissue-specific proteins and the like.

Sub-tissue distribution, such as in particular cells, organelles, fractions and so on also can be examined. The tissue is treated to release the individual component cell or cells; the cells are treated to release the individual component organelles and so on. Those partitioned samples then can serve as the protein source for discrimination in 2-D gels and any further methodologies associated therewith.

In the case of a tissue, a tissue sample is obtained and prepared for separation of the proteins therein using a method that provides suitable levels of discrimination of the proteins comprising a cell. The proteins can be obtained by any of a variety known means, such as enzymatic and other chemical treatment, freeze drying the tissues, with or without a solubilizing solution, repeated freeze/thaw treatments, mechanical treatments, combining a mechanical and chemical treatment and using frozen tissue samples and so on.

To provide a more particularized origin of protein, specific kinds of cells can be purified from a tissue using known materials and methods. To provide proteins specific for an organelle, the organelles can be partitioned, for example, by selective digestion of unwanted organelles, density gradient centrifugation or other forms of separation, and then the organdies are treated to release the proteins therein and thereof. The cells or subcellular components are lysed as described hereinabove. Other specific techniques for isolating single cells or specific cells are known such as Emmert-Buck et al., "Laser Capture Microdissection" Science 274 (5289):998–1001 (1996).

Sensitive methods for cell separation may involve the use of cell type-specific antibodies attached to magnetic beads. Such beads have been used to isolate cholangiocytes for high-resolution protein analysis. (Cholangiocyte-specific rat liver proteins identified by establishment of a two-dimensional gel protein database. Tietz et al., Electrophoresis 19:3207–3212, 1998). Systematic development of magnetic bead cell separation requires the isolation of cell type-specific proteins from the cell membranes of as many human cells as possible. Thus, knowledge of the tissue, cell or fraction specific proteins is important to cell fractionation systems.

Complete, perfect separation of subcellular particles and of different cell types is difficult and varying levels of contamination frequently will be seen. In addition, instances can occur where two or more cell types are very difficult to separate without much further development. In such instances, methods for the decomposition of mixtures based on the analysis of mixtures containing different ratios of two cells may be used. The principles of mixture decomposition applied to the analysis of two-dimensional electrophoretic separation of protein samples have been mentioned in Taylor & Giometti, Appl. Theor. Electrophoresis 1:47–51, 1988. Such methods can be applied to subcellular fraction analysis or to the deconvolution of mixtures of three or more cell types in the instant invention.

Subcellular fractionation using density gradients and zonal centrifuges has been described (Anderson, "The Development of Zonal Centrifuges and Ancillary Systems for Tissue Fractionation and Analysis" National Cancer Institute Monograph 21, 1966). A variety of methods have been developed aimed at the isolation of one or more subcellular fractions. However, multiple parallel methods wherein a series of similar samples, for example, liver samples from different individuals, are fractionated in parallel wherein all of the initial sample is recovered and which are therefore quantitative, have not been described previously nor has any need existed for such methods to be developed. In the instant invention, reproducible density gradients and attending materials and methods for 2-D gel electrophoresis are formed by the materials and methods of related patent applications, Ser. Nos. 551,314 filed Apr. 18,2000; 628,340 filed Jul. 28, 2000; 573,539 filed May 19, 2000; and 643,675 filed Aug. 24, 2000; as well as attorney docket numbers 40148 filed Jul. 21, 2000 relating to automated SDS electrophoresis, the contents of which are incorporated by reference. Those techniques allow minor proteins concentrated in one or a few subcellular fractions to be identified and quantitated. Thus, the dynamic range of the two dimensional gel electrophoresis (2DE) analysis or other analysis is greatly increased to the level where a comprehensive protein database now can be generated.

In 2DE maps of whole tissues, a few proteins are observed which are restricted to one subcellular fraction. For example, the mitochondrial proteins, HSP 60 and COX-II, and the nuclear proteins, PCNA and LAM-B, are seen on 2D gels, while dozens of minor proteins in those organelles are not. The minor proteins are seen, however, when isolated mitochondria or nuclei are analyzed separately. An alternative method for increasing the dynamic range while preserving quantitation is to use one or a few proteins for quantitative referencing. The amount of lamin-B, for example, can be determined in a gel pattern from a whole tissue, and in a gel pattern obtained using highly purified nuclei. In the first pattern, lamin B will be a minor spot, in the latter, a major spot. The ratio of spot intensity for protein of isolated nuclei may be referenced to lamin B. The ratio between the lamin B intensity on whole tissue gels and on the gels from isolated nuclei can be used as a multiplier to calculate the quantity of minor proteins in the whole tissue sample. That spot intensity referencing technique can be applied to any other organelle or source wherein minor proteins are to be identified.

The lysate can be treated to remove non-proteinaceous matter by particular treatments, such as digestion with a nuclease or a lipase. The unwanted molecules then can be removed by, for example, physical means, such as, centrifugation, precipitation and so on.

The crude protein preparation can be treated further to enhance the purity of the proteins. The crude protein preparation also can be exposed to a treatment that partitions the proteins based on a common property, such as size, subcellular location and so on.

For example, the crude lysate can be partitioned prior to high-resolution separation of the proteins to reduce the number of proteins for ultimate separation and to enhance discrimination. Thus, the crude lysate can be fractionated by chromatography. Such a preliminary treatment is particularly useful when a sample is known to contain one or more abundant proteins, such as, albumin in serum. Removing abundant proteins may enhance the relative abundance of minor species of proteins that can be loaded on a 2-DG. Plural preliminary fractionation steps can be practiced, such as, using multiple chromatography steps, with the chromatography steps being the same or different, or multiple extraction or other partitioning steps. Suitable chromatography methods include those known in the art, such as immunoaffinity, size exclusion, lectin affinity and so on.

In the experiments yielding the serum protein data given in some of the figures, the five abundant serum proteins, albumin, transferrin, haptoglobin, alpha-1-antitrypsin and IgG were removed by passing the sample through a column having an immobilized antibody to each of those proteins. The process removed over 80% of the proteins and allowed higher gel loading of less common proteins. Additional data has been generated using 11 antibodies to the common serum proteins thereby removing 93% of the more abundant proteins. That immunosubtracting method thus relies on the concurrent use in a single step of multiple, immobilized antibodies to the more common proteins.

The proteins then are separated by a method that provides discrimination and resolution. For example, the proteins can be separated by known methods, such as chromatography, immunoelectrophoresis, mass spectrometry or electrophoresis. The proteins can be separated in a liquid phase in combination with a solid phase. For example, a suitable separation method is two-dimensional (2-D) gel electrophoresis.

Figure 2:
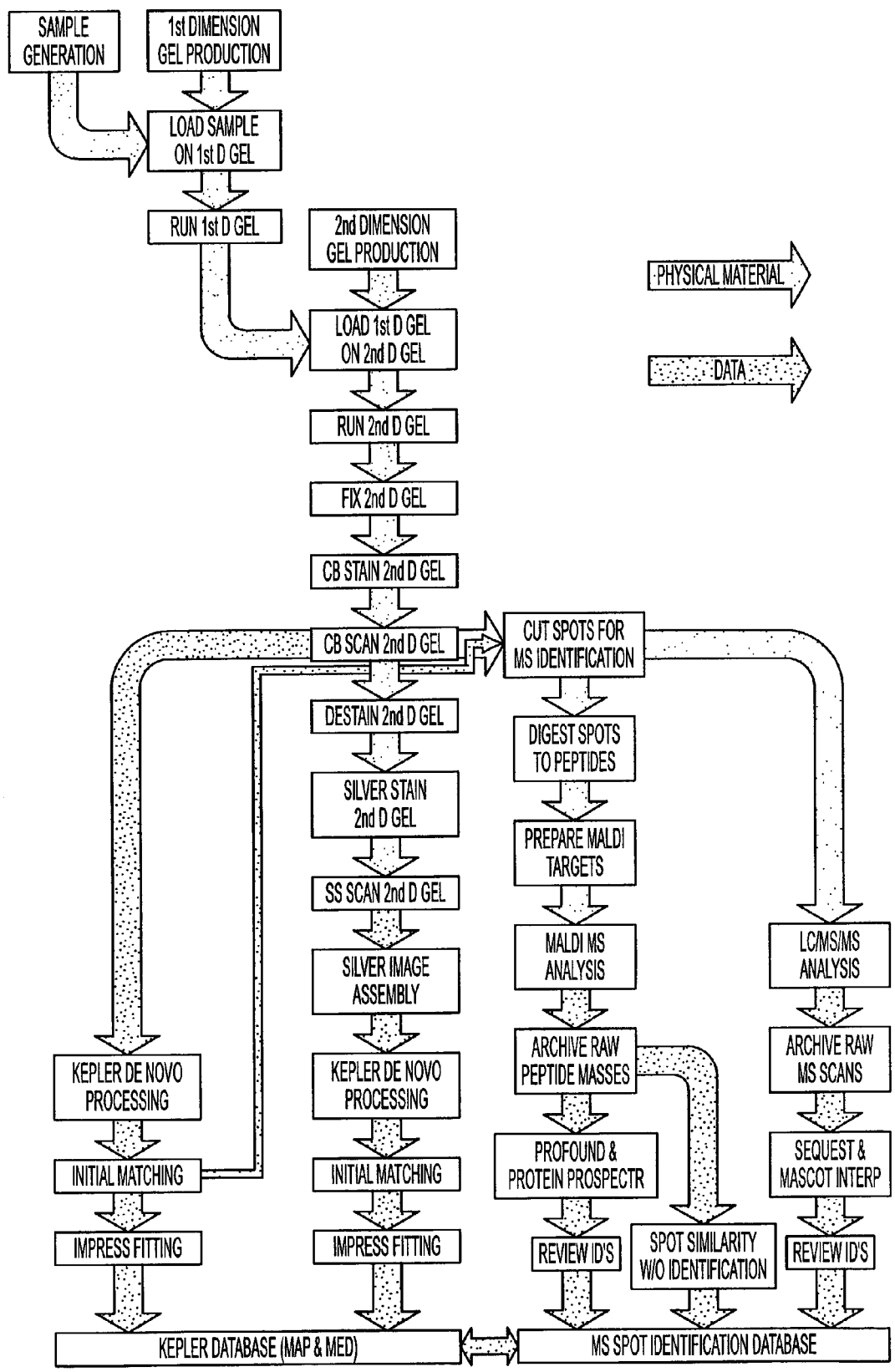
FIG. 2 is a more detailed schematic block diagram showing various steps in the analysis depicted in FIG. 1, the steps depicted in FIG. 2 being directed to an analysis of one tissue sample at a time.

An overall scheme employing 2-D gel electrophoresis for the initial separation of proteins is provided in FIGS. 1 and 2.

The blocks in FIG. 1 indicate the following steps:

Scan 2D Gel A (B) of Tissue A (B): represents the steps of operating a camera or scanner to scan a 2 dimension electrophoresis gel produced in the steps set forth in FIG. 2, the scanned image then being inputted into a computer for computer analysis;

Locate Spots via Image Processing: represents the steps of performing a computer analysis of the spots that appear in the scanned image of the 2D gel to identify location and size of each spot in the 2D gel and thereafter select specific spots to be excised for further study by, for instance, mass spectrometry;

Cut Spots for MS (Mass Spectrometry) Identification: represents the step of excising spots from the 2D gel that have been identified as being designated for further study;

Digest Spots to Peptides: represents well know procedures for processing excised spots in preparation of mass spectrometry analysis;

Prepare MALDI TARGETS: represents spotting or depositing the digested spots from the 2D gel on a MALDI mass spectrometry sample plate;

MALDI MS Analysis: represents the performance of a mass spectrometry analysis on each digested spot on the sample plate using a MALDI-TOF mass spectrometry apparatus (a matrix-assisted laser desorption ionization apparatus) where the biological sample is embedded in a volatile matrix and is vaporized by being subjected to an intense laser emission—one such MALDI apparatus being a MALDI-TOF apparatus (TOF is time-of-flight spectrometry), the results of the analysis being the mass of the peptides of the tested processed spot samples;

Archive Raw Peptide Masses: represents storage in either or both computer format and paper archive format of the results of the MALDI mass spectrometry analysis;

Spot # Peptide #: represents the step of comparing the various determined masses (molecular weight MW) of the peptides analyzed using the mass spectrometry apparatus, the peptides of tissue A being compared to the peptides of tissue B;

Generate Similarity Scores For All Gel A Spot Peptide Masses vs. All Gel B spot Peptide Masses: represents the step of generating and storing the results of the comparison between the peptide masses of the spots of the 2D gel of tissue A and the peptide masses of the spots of the 2D gel of tissue B;

Select Similarities Above Threshold Likely To Indicate Protein Identity: represents the steps of selecting those generated similarities in peptide masses (MW) that clearly indicate a correspondence between spots in the 2D gel of tissue A and the 2D gel of tissue B;

Retain Putative Matches Where Gel A Spot and Gel B Spot Have Similar pI, MW: represents the storage of the selected similarities between gel A and gel B, wherein pI represents the isoelectric focusing point of each protein separated during electrophoresis;

Gel A Spot 1—Gel B Spot 25 . . . : represents a list of the retained putative matches between spots in gel A and spots in gel B;

Warp Gel A onto Gel B Using MS Matches as Landmark Matches: represents a computer implemented process whereby the spots in the scanned computer image of gel A are warped into alignment (registration) with the spots in the scanned computer image of gel B (Warping refers to a process of applying geometric corrections to modify the shape of features and to change their spatial relationships. Warp is a statistical treatment of the multiple elements of plural arrays to yield a best fit of the arrays. Another term used for a warping process is rubber-sheeting because the warping process can be likened to stretching a rubber sheet wherein portions of one or more images are stretched or shrunk in order to bring the spots on all the images into registration with one another and still maintain relative positional relationships between the spots.);

Match Additional Spots Based Upon Positional Similarity After Warping: represents the steps of matching additional spots based on similar relative locations of the spots in gel B with the locations in the spots in warped gel A;

Verify Additional Matches Using MS Data: Marginal Similarity: represents the steps of performing additional mass spectrometry (MS) analysis of several spots that are in marginally similar locations in the gel B and warped gel A in order to verify that the various spots are indeed the same peptides in each of the two gels; and Homologous Spots Identified, Unmatched Spots Classed as Unique: represents the steps of concluding that all landmark matches, all matched spots, all aligned spots and all verified matched spots are indeed the same spots common to both gel A and gel B thereby providing a relationship between a plurality of the peptides (proteins) in tissue A and tissue B, and further classifying all unmatched spots in gels A and B as being unique to respective tissue A or tissue B.

The blocks in FIG. 2 represent the following steps:

Sample Generation: represents known methods of preparing a sample from a biological tissue for subsequent electrophoresis;

$1^{st}$ Dimension Gel Production: represents known methods of preparing a gel for use in a first dimension of electrophoresis;

Load Sample on 1$^{st}$ D Gel: represents the step of depositing the prepared sample into the first dimension electrophoresis gel;

Run 1$^{st}$ D Gel: represents subjecting the first dimension electrophoresis gel to predetermined amounts of electric current to separate the prepared sample linearly along the length of the 1$^{st}$ D gel;

2$^{nd}$ Dimension Gel Production: represents the steps of preparing a 2 dimension electrophoresis gel;

Load 1$^{st}$ D Gel On 2$^{nd}$ D gel: represents the step of taking the 1$^{st}$ D gel with the separated sample and depositing the 1$^{st}$ dimension gel on one edge of the 2$^{nd}$ D gel;

Run 2$^{nd}$ D Gel: represents the step of subjecting the 2$^{nd}$ D gel to a predetermined amount of electric current to further separate the proteins from the 1$^{st}$ D gel into a planar two dimensional array of separated proteins;

Fix 2$^{nd}$ D Gel: represents the steps of removing the 2$^{nd}$ D gel from retaining glass plates that supported the 2$^{nd}$ D gel during the current applying process (the electrophoresis) and thereafter treating the gel with affixing solution in preparation for further processing:

CB Stain 2$^{nd}$ D Gel: represents various steps necessary for staining the spots on the 2$^{nd}$ D gel using Coomasie blue dye (CB) thereby making the spots visible;

CB Scan 2$^{nd}$ D Gel: represents the scanning process mentioned with respect to FIG. 1, whereby the 2$^{nd}$ D gel is scanned by a scanner or a camera to generate a computer processable image of the gel;

Destain 2$^{nd}$ D Gel: represents the process of removing stain from the gel;

Silver Stain 2$^{nd}$ D gel: represents the step of restaining the gel using a silver stain;

SS Scan 2$^{nd}$ D Gel: represents the step of scanning the silver stained 2$^{nd}$ D gel using a camera or scanner, where optionally multiple time-lapse scans of a single gel may be taken during the staining process;

Silver Image Assembly: represents the process of combining multiple images of a single gel to obtain more refined information as set forth in co-pending U.S. Ser. No. 09/387,728 filed Sep. 1, 1999 entitled "Gel Electrophoresis Image Combining . . . " incorporated herein by reference in its entirety; Kepler De Novo Processing: represents the step of subjecting the silver stain image of the gel being processed using the KEPLER™ software or other similar spot analyzing software (KEPLER™ is the trade name of a data collection, collation and storage means beginning with image analysis of stained gels and including transformation of that data into a digitized form);

Initial Matching: represents the step of manually (visually) identifying various spots in the gel image;

Impress Fitting: represents a computer implemented process whereby spots in the scanned gel image are processed in conjunction with manipulation of a tissue-specific master pattern, the master pattern defined relative locations of various spots and having master spot numbers that identify previously considered spots, the process being performed to identify various spots in the scanned 2$^{nd}$ D gel to assign master spot numbers to at least some of those identified spots—the Impress process being disclosed in co-pending U.S. patent application entitled "Method and Apparatus for Impressing a Master Pattern to a Gel Image" filed Aug. 31, 2000 having attorney docket number 40732, incorporated herein by reference in its entirety;

Kepler Database (MAP & MED): represents the step of updating the Kepler database, including the sections of the data base MAP (Molecular Anatomy and Pathology) and MED (Molecular Effects of Drugs);

Cut Spots for MS Identification: represents the steps of locating and excising various spots that are to be subsequently analyzed using a mass spectrometer—one spot cutting (excising) apparatus being disclosed in U.S. Pat. No. 5,993,627 incorporated herein by reference in its entirety;

Digest Spots: represents the step mentioned above with respect to FIG. 1 where spots excised from the 2$^{nd}$ D gel are processed in preparation for MS analysis;

Prepare MALDI Targets: represents the step mentioned above with respect to FIG. 1 where digested spots are deposited on a sample plate of a MALDI mass spectrometry apparatus;

MALDI MS Analysis: represents the step of analyzing spots using a MALDI mass spectrometry apparatus as mentioned above with respect to FIG. 1;

Archive Raw Peptide Masses: represents the step mentioned above with respect to FIG. 1, wherein the masses (molecular weights) of the peptides subjected to MS analysis are stored;

Profound & Protein Prospectr represent the steps of comparing the analysis results using two commercially available software programs, PROFOUND marketed by Proteometrics, Inc. and PROTEIN PROSPECTR marked by Applied Biosystems, Inc.;

Review Ids: represents a review of the various spot identifications described above;

MS Spot Identification Database: represents the updating of a database having compiled mass spectrometry data therein;

Spot Similarity w/o Identification: represents the step of adding various hypothetical identifications of spots to the MS Spot Identification Database concerning various spots that were not subjected to MS analysis but where the hypothetically identified spots did fall into alignment with spots from a different tissue sample 2$^{nd}$ D gel;

LC/MS/MS Analysis: represents various additional analysis steps, including liquid chromatography processes (LC) and tandem mass spectrometry processes (MS/MS);

Archive Raw MS Scans: represents the step of storing for future consideration the results of all mass spectrometry tests; and Sequest & Mascot Interp: represents the steps of interpreting the analysis results using commercially available software programs with SEQUEST being commercially available from Finnegan and MASCOT from Micromass.

Methods for cell separations from tissues for a limited number of cell types are known, as are means for subcellular fractionation of certain components, many of which are specific to one tissue or cell type. Separation reagents and methods were not previously available that are applicable to the separation of every human cell type. No multiple-parallel high-resolution methods for subcellular fractionation of many samples of different cells or tissues have been previously described nor was any such separation methodology ever needed or desired previously.

Means for the partial global separation of cell proteins using high resolution two-dimensional electrophoresis are known, as are methods and systems for characterizing, sequencing and identifying the separated proteins by mass spectrometric methods. However, those techniques, from cell separation through to protein identification have not been integrated into one automated system capable of high throughput. Organ-specific and cell-specific proteins also are well known, but no complete index of such has been attempted.

In general, 2-D gel electrophoresis separates proteins by charge and molecular weight (MW). The two parameters on which 2-D separation is based, namely isoelectric point and mass, are almost completely unrelated. Thus, the theoretical resolution of the 2-D system is the product of the resolutions of each of the constituent methods, which is in the range of 150 molecular species for each of isoelectric focusing (IEF) and of sodium dodecyl sulfate (SDS) gel electrophoresis. Hence, the theoretical resolution for the complete system is about 22,500 proteins. In practice, as many as 5,000 proteins have been resolved experimentally. Resolution can be enhanced by the selective use of sample, reproducible and standardized methods and sensitive detection means, for example.

The solid phase gels for 2-D electrophoresis generally are made of a porous polymer, such as polyacrylamide, and are constructed using known methods. To minimize interassay and intraassay variability, it is beneficial if the materials and methods for making the gels are reproducible and perhaps, produced by an automated means to reduce introduced variability. Gel monomers are mixed with agents that induce polymerization and then are poured into a mold that dictates the size and shape of the polymerized gel. For example, the catalyzed liquid gel monomer can be poured between glass plates separated uniformly over the entire surfaces thereof to produce a square or rectangular slab gel. The glass plates can be separated by about a millimeter or a fraction thereof. Thinner gels generally enhance resolution.

Protein samples to be analyzed using 2-D electrophoresis typically are solubilized in an aqueous, denaturing solution such as one containing a chaotropic agent, such as, urea, at a concentration of about 9 M; a detergent, and perhaps a non-ionic detergent, such as, NP-40, at a concentration of about 2%; a commercially available set of ampholytes, often purchased as a mixture, for example of a defined pH range of 8 to 10; and a reducing agent, such as, dithiothreitol (DTT), at a concentration of about 1%. The solubilization step may be separated into different stages each with different solubilizing solutions to prepare different fractions to further distinguish the proteins.

The chaotropic agent and detergent dissociate complexes of proteins with other proteins and with DNA, RNA etc. A suitable ampholyte mixture is one that serves to establish a high pH (~9) outside the range where most proteolytic enzymes are active, thereby preventing modification of the sample proteins by such enzymes in the sample. The high pH ampholytes complex with DNA present in the sample. By complexing the DNA, the ampholytes allow DNA-binding proteins to be released while preventing the DNA from swelling into a viscous gel that interferes with separation. The reducing agent minimizes the presence of disulfide bonds in the sample proteins, thus allowing the proteins to be unfolded and to assume an open structure optimal for separation.

Samples of tissues, for example, are solubilized by rapid homogenization in various denaturing, solubilizing solution (s), after which the sample is centrifuged to pellet insoluble material and DNA. The supernatant is collected and is amenable to the separation procedure.

To ensure that proteins retain constant chemical properties during separation, it is desirable that the sulfhydryl (SH) groups of the cysteine residues do not reform disulfide bridges or become oxidized to cystic acid. Therefore, cysteine residues can be rendered stable by various modifications of the sulfhydryl groups, for example, by alkylation with a zwitterionic derivative of iodoacetamide (2-amino-5-iodoacetamido-pentanoic acid). That reaction introduces a very hydrophilic group on the cysteine residues but does not change the net charge or apparent isoelectric point of the polypeptide.

Such a derivatization can be implemented, for example, using a size exclusion gel filtration column to exchange the proteins out of the initial sample solubilization solution, through a reagent zone containing, for example, an alkylating reagent, and finally into a medium suitable for application to an IEF gel. The size exclusion medium can be chosen to exclude proteins but not low molecular weight solvents (e.g., polyacrylamide beads such as BioRad P-6 BioGel).

Of the 20 amino acids found in typical proteins, four (aspartic and glutamic acids, cysteine and tyrosine) carry a negative charge and three carry a positive charge (lysine, arginine and histidine) in some pH range. A specific protein, defined by the specific sequence of amino acids thereof, thus is likely to incorporate a number of charged groups therein. The magnitude of the charge contributed by each amino acid is governed by the prevailing pH of the surrounding solution and can vary from a minimum of 0 to a maximum of 1 charge (positive or negative depending on the amino acid) as revealed in a titration curve relating charge and pH according to the pK of the amino acid in question. The total charge of the protein molecule is, under denaturing conditions, approximately the sum of the charges of the component amino acids, all at the prevailing solution pH.

Two proteins having different ratios of charged, or titrating, amino acids can be separated by virtue of different net charges at some pH. Under the influence of an applied electric field, a more highly charged protein will move faster through a medium than a less highly charged protein of similar size and shape. If the proteins thus are made to move from a sample zone through a non-convecting medium, such as, a polyacrylamide gel, an electrophoretic separation will result. If, in the course of migrating under an applied electric field, a protein enters a region whose pH has that value at which the net charge of the protein is zero, that is, the isoelectric pH or isoelectric point, the protein will cease to migrate relative to the medium. Further, if the migration occurs through a monotonic pH gradient, the protein will 'focus' at the particular pH value where movement is minimal.

If the protein moves toward more acidic pH values, the protein will become more positively charged and a properly oriented electric field will propel the protein back towards the isoelectric point. Likewise, if the protein moves towards more basic pH values, it will become more negatively charged and the same field will drive the protein back toward the isoelectric point.

The isoelectric focusing separation process can resolve two proteins differing by less than a single charged amino acid among hundreds in the respective primary amino acid sequences.

Formation of an appropriate spatial pH gradient is a requirement of the focusing procedure. That can be achieved either dynamically, by including a heterogeneous mixture of charged molecules (ampholytes) in the initially homogeneous separation medium, or statically, by incorporating a spatial gradient of titrating groups into the matrix through which the migration will occur. The former represents classical ampholyte-based isoelectric focusing, and the latter, the more recently developed immobilized pH gradient (IPG) isoelectric focusing technique.

The IPG approach has the advantage that the pH gradient is fixed in the gel, while the ampholyte-based approach is susceptible to positional drift as the ampholyte molecules move in the applied electric field. In practice, the two approaches can be combined to provide a system where the pH gradient is spatially fixed, but small amounts of ampholytes are present to decrease the adsorption of proteins onto the charged matrix containing the IPG.

IPG gels can be created in a thin planar configuration bonded to an inert substrate, such as, a sheet of Mylar plastic that has been treated so as to bond chemically to an acrylamide gel (e.g., Gelbond® PAG film, FMC Corporation). The IPG gel typically is formed as a rectangular plate about 0.5 mm thick, 10 to 30 cm long (in the direction of separation) and about 10 cm wide.

Multiple samples can be applied to such a gel in parallel lanes. However, the ability to separate plural samples must be balanced with the attending problem of diffusion of proteins between lanes.

When one or more of the separated proteins in a given lane are to be recovered from that lane following focusing, as is typically the case in 2-D electrophoresis, it may prove beneficial to split the gel into narrow strips, such as, about 3 mm wide strips, each of which can be run as a separate gel. Since the proteins of a sample then are confined to the volume of the gel represented by the single strip, quantitative recovery of the separated proteins in that strip can be obtained. Such strips are produced commercially, for example, by Pharmacia (Immobiline DryStrips).

While the narrow strip format solves the problem of containing samples within a recoverable, non-cross-contaminating region, there remain other considerations associated with the introduction of sample proteins into the gel. Since protein-containing samples typically are prepared in a liquid form, the proteins must migrate, under the influence of the electric field, from a liquid-holding region into the IPG gel to undergo separation. Thus, for example, the IPG strip can be reswollen, from the dry state, in a solution containing sample proteins, with the intention that the sample proteins completely permeate the gel at the start of the run.

Suitable compositions of the components combined to make a focusing gel are known in the art. Solutions of polymerization catalyst and initiator (assuming that each comprises about 10% of the total volume dispensed) can be, respectively, about 1.2% tetramethylethylene diamine (TEMED) and about 1.2% ammonium persulfate (AP), both in water. The two solutions of polymerizable monomers (whose proportions in the output stream vary to yield a gradient of titratable monomers and physical density) may be made to achieve a gradient over the pH range of about pH 4 to 9. The titratable monomers used can be, for example, Immobilines® manufactured by Pharmacia Biotech. Glycerol and deuterium oxide (heavy water) can be used to increase the density of one of the solutions, thereby helping to stabilize the gradient formed in the mold through the interaction of the resulting density gradient and ambient gravity.

After sample loading, the gel strip is exposed to a device to effect focusing, for example, the gel strip is moved to one of a plurality of slots filled with, for example, a non-conducting oil, such as silicone oil, and having slotted carbon electrodes at both ends positioned so as to contact the ends of the gel. The oil may be circulated, cooled to ensure constant running temperature and sparged with a dry gas to eliminate oxygen and dissolved water. Since the resistance of the gel rises during the run, slots maintained at a series of different voltages are provided, and the strip is moved from one voltage to a higher voltage as the run progresses. For example, a series of voltage stages can be provided, for example, 1, 2.5, 5, 10, 20 and 40 kilovolts. The gel can be maintained at each voltage for about 3 hours, except at the last voltage, where the gel can rest until a second dimension slab gel is available. A total of 200,000 to 300,000 volt-hours may be applied to each gel.

During the early stages of a separation run, under an applied electric field, proteins can migrate through the liquid phase of the applied sample along a pH gradient initially formed by the action of the ampholytes incorporated in the sample. Because the proteins initially are migrating through liquid, without the retardation associated with migration through a gel matrix, the proteins can approach individual isoelectric points more rapidly than in a system where the entire migration path is through a gel.

As the run progresses, the sample-containing liquid is imbibed by the gel, progressively shrinking the channel so that at the end of the run, the channel contains a negligible amount of liquid. That can be achieved by allowing surface water to be removed slowly from the exterior surface of the gel during the run, for example, by immersion of the gel in circulated silicone oil that has been dehydrated by sparging with a dry gas such as argon or nitrogen.

During gel dehydration, proteins enter the gel at positions near the respective isoelectric points of the proteins. Thus a mixture of different proteins will enter the gel at points distributed along the gel length, rather than at one site at the edge of a sample well, thereby avoiding the precipitation often observed when a complex mixture of proteins migrate into a gel together through a small gel surface area. Excess liquid is removed through the exterior gel surface, either to a dry gas phase or to a water-extracting non-aqueous non-conducting liquid phase such as silicone oil.

Isoelectric focusing and various aspects of gel electrophoresis separation techniques are described, for example, in U.S. Pat. Nos. 4,130,470; 4,196,036; 4,594,064; 5,074,981; 5,164,065; 5,275,710; and 5,304,292.

In a 2-D procedure, once the proteins are separated according to isoelectric point, the proteins generally then are separated by size.

The proteins can be native and untreated or treated with a detergent or other reagent that causes the proteins to assume a uniform shape so that the separation is based solely on size. For example, the proteins can be denatured by treatment with a detergent, such as, sodium dodecyl sulfate (SDS).

Charged detergents such as SDS bind strongly to protein molecules and unfold the proteins into semi-rigid rods where the length thereof is proportional to the length of the polypeptide chain and hence approximately proportional to molecular weight. A protein complexed with such a detergent also is highly charged (because of the charges of the bound detergent molecules) and that charge causes the complex to move in the applied electric field.

Furthermore, the total charge is approximately proportional to molecular weight since the charge of the detergent vastly exceeds the intrinsic charge of the protein and hence the charge per unit length of a protein-SDS complex is essentially independent of molecular weight. That feature renders protein-SDS complexes essentially equal in electrophoretic mobility in a non-restrictive medium. If, however, the migration occurs in a sieving medium, such as a polyacrylamide gel, large (long) molecules will be retarded as compared to small (short) molecules, and a separation based approximately on molecular weight can be achieved. That is the principal of SDS electrophoresis as applied commonly to the analytical separation of proteins.

An important application of SDS electrophoresis involves the use of a slab-shaped electrophoresis gel as the second dimension of a two-dimensional procedure. The gel strip or cylinder in which the protein sample has been resolved by isoelectric focusing is placed along the slab gel edge and the molecules are separated in the slab, perpendicular to the prior separation, to yield a two-dimensional separation.

It is current practice to mold electrophoresis slab gels between two glass plates, and then to load sample and to run the slab gel still between the same glass plates. The gel is molded by introducing a dissolved mixture of polymerizable monomers, catalyst and initiator into the cavity defined by the plates and spacers or gaskets sealing three sides. Polymerization of the monomers then produces the desired gel medium. The gasket or form comprising the "bottom" of the molding cavity is removed after gel polymerization to allow current to pass through two opposite edges of the gel slab: one of the edges represents the open (top) surface of the gel cavity, and the other is formed against the removable bottom. Typically the gel is removed from the cassette defined by the glass plates after the electrophoresis separation has taken place, for purposes of staining, autoradiography etc., required for detection of resolved proteins.

The concentrations of polyacrylamide gels used in electrophoresis are generally stated in terms of %T (the total percentage of acrylamide in the gel by weight) and %C (the proportion of the total acrylamide that is accounted for by the crosslinker used). N,N'-methylenebisacrylamide ("bis") is a typically used crosslinker.

In most conventional systems of SDS electrophoresis, use is made of the stacking phenomenon. In a stacking system, an additional gel phase of high porosity is interposed between the separating gel and the sample. Further, the two gels initially contain a different mobile ion from the ion source (typically a liquid buffer reservoir) above the gels. Thus, the gels contain, for example, chloride (a high mobility ion) and the buffer reservoir contains, for example, glycine (a lower mobility ion, whose mobility is pH dependent).

All phases generally contain a known buffer, such as, Tris, as the low-mobility, pH determining buffer component and positive counter ion. Negatively charged protein-SDS complexes present in the sample are electrophoresed first through the stacking gel at a pH of approximately 6.8, where the complexes have the same mobility as the boundary between the leading (for example, $Cl^-$) and trailing (for example, $glycine^-$) ions. The proteins are thus "stacked" into a very thin zone sandwiched between the $Cl^-$ and $glycine^-$ zones.

As the stacking boundary reaches the top of the separating gel, the proteins become unstacked because at the higher separating gel pH (8.6), the protein-SDS complexes have a lower mobility. Thus in the separating gel, the proteins fall behind the stacking front and are separated from one another according to size as the proteins migrate through the sieving environment of the lower porosity (higher %T acrylamide) separating gel.

Running slab gels can take, for example, one of two modes. A gel in a cassette typically is mounted on a suitable electrophoresis apparatus so that one edge of the gel contacts a first buffer reservoir containing an electrode (typically a platinum wire) and the opposite gel edge contacts a second reservoir with a second electrode, steps being taken so that the current passing between the electrodes is confined to run mainly or exclusively through the gel. Such apparatus may be "vertical" in that the upper edge of the gel is in contact with an upper buffer reservoir and the lower edge is in contact with a lower reservoir, or the gel may be rotated 90° about an axis perpendicular to a plane, and the gel is run horizontally between a left and right buffer reservoir. Various other configurations have been devised to make the connections electrically and to simultaneously prevent liquid leakage from one reservoir to the other (around the gel).

When used as part of a typical 2-D procedure, an IEF gel is applied along one exposed edge of such a slab gel and the proteins within migrate into the slab gel under the influence of an applied electric field. The IEF gel may be equilibrated with solutions containing, for example, SDS, buffer and reducing agents, prior to placement on the SDS gel to ensure that the proteins in the IEF gel are prepared to migrate under optimal conditions. Alternatively, the equilibration may be performed in situ by surrounding the gel with a solution or gel containing the components after which the gel is placed in position along the edge of the sizing gel.

Gel electrophoresis to size proteins, and the various modifications to the basic materials and methods, has been described for example, in U.S. Pat. Nos. 4,169,036; 4,594,064; 4,839,016; 5,074,981; 5,209,831; 5,217,591; 5,275,710; and 5,306,404.

Because there may be limitations in the degree of resolution and discrimination of proteins in a gel, various manipulations can be implemented to optimize the information that can be obtained. For example, individual gels can be configured so that particular and more limited pH ranges are represented. Thus, a gel can contain a range of pH values from 7 through 14, or can contain a range of only three to four pH units that will provide greater separation within one pH unit.

For larger molecules, the configuration of the matrix can be modified to enable separation thereof. For example, a lower concentration of monomer resulting in a more porous gel can be used. In addition, gels of normal concentration and separation resolution can be used, but the proteins can be partially broken down by digestion to provide a subset of smaller component polypeptides. The artisan can develop such modifications based on the prevailing methodologies.

Some proteins may not be amenable to good separation and resolution in 2-D electrophoresis, for example, because of extreme hydrophobicity and/or insolubility in the detergents/solvents used in 2-D gels. Examples are the hydrophobic membrane proteins. In that event, alternative procedures are available. For example, the proteins can be treated repeatedly with a solution compatible with 2-D electrophoresis, such as, a buffer containing urea, NP-40, DTT and ampholytes. The insoluble proteins are removed, for example, by centrifugation and the supernatant collected.

Alternatively, an extraction can be performed using an organic solvent. The treated proteins then are applied to a suitable fractionation system, such as, SDS gel electrophoresis, with or without heating in SDS buffer or chromatography in an organic solvent, such as methylene chloride or acetonitrile. The resulting separated proteins are quantified, for example, by optical absorbance, and then should be amenable for further analysis.

To visualize the separated proteins that normally form spots or smears of varying concentration based on molecular weight and charge, or are isolated at particular sites in the gel, the proteins are treated or are stained to be made detectable. For example, the proteins can be stained with a generalized dye that binds non-specifically to proteins, such as Coomasie Blue or a silver-based compound. Alternatively, negative staining can be practiced, for example by using a zinc salt that precipitates SDS in areas lacking protein. The reagents and methods are commercially available. Other protein stains are known in the art, such as fluorescent stains, SYPRO Red (Molecular Probes Corp., Oregon) and so on. Other detecting means include using antibodies, particularly labeled antibodies, to identify proteins. A single gel may be stained multiple times, with optional destaining procedures interspersed.

Thus, for example, in the case of positive protein staining, in a first tank, the gel is immersed up to the stacking gel in a solution comprising for example about 50% alcohol, such as ethanol, about 2% phosphoric acid and water for a period of about two hours to fix the proteins in place and to remove most of the buffer components, such as SDS, Tris and glycine, in the gel. Following fixation, the gel is moved to a tank containing, for example, about 28% methanol, about 14% ammonium sulfate and about 2% phosphoric acid in water and incubated for about two hours. Next, the gel is moved to a tank containing the same solution with the addition of powdered Coomassie Blue G250 dye, the whole liquid volume being circulated continually in the tank. The dye permeates the gel, binding to resolved protein spots. Finally, the gel is removed from that tank.

A feature of the instant invention is the detailed analysis of the molecular weight and isoelectric point (pI) of the protein. Individual gels are analyzed so that a detailed description of the discriminated proteins can be obtained. A suitable means to obtain such information is to have the information of each protein cataloged and stored in a data storage means. A computerized means for scanning, digitizing, processing, analyzing and storing the information is a preferred way for extracting that information and having the information available in a manner for ready comparisons. Thus, an electronic image of the stained gel is obtained. One example, is scanning the gel. To maximize the information for each protein, a gel can be exposed to multiple subsequent staining procedures. Thus, for example, a low sensitivity stain, such as Coomassie Blue, can be followed by a stain of greater sensitivity, such as a silver stain. The scanning, analyzing and storing of information preferably occurs after each staining procedure.

Moreover, multiple sequential scans can be performed to obtain further information. Such information can yield enhanced precision and dynamic range of such non-equilibrium stains, such as a silver stain. In such circumstances, the development process yields spots that stain intensely, moderately and at a very low level. By taking multiple sequential scans, spot quantification can be based on measurement parameters other than optical density, such as maximum rate of change of absorbance and time of onset of development. Also, proteins may be colored differently based on known or unknown reasons. In any event, any such distinction can serve as a diagnostic identifying parameter of a protein.

A suitable means for obtaining the raw information for further data analysis would be to scan the pattern of discriminated proteins in a gel by an image processing means to yield a digitized image. Scanning can be performed by gently laying the gel on a horizontal vertical or tilted illuminating table. An overhead digital camera, such as a CCD digitizer, then is used to acquire an image of the gel and the stained protein spots in absorbance mode. Alternative scanning modes may be practiced for measuring fluorescence or light scattering, depending on the stain used.

The data obtained from the scanning means then is transferred to a data inputting means and storage means for ordered archiving of the data relating to the individual proteins and spots. Scanned images of 2D protein patterns can be subjected to an automated image analysis procedure using batch process computer software, such as the Kepler® system that subtracts image background, and detects and quantifies spots. The final data for a 2-D gel, a series of records describing position and abundance for each spot, among other distinguishing features, then are inserted as records in a computerized relational database.

The storage of data and the comparisons between and among proteins is accomplished with a data processing means. A data storage means archives the data on each of the protein spots on a storage medium. The digitized data can be transformed, filtered, enhanced and so on to clarify the scanned plot of protein data and information provided for each protein or spot noted on the gels. The storage means that compiles and contains an ordered array of the protein information, such as the various parameters and characteristics thereof, can be any known means including, a printed medium, such as a book or table, or a computer readable means, such as a compilation of data stored on a diskette, compact disc and so on.

One of the ways to index the proteins is to characterize each individual protein based on the properties thereof, such as molecular weight, isoelectric point (pI), tissue distribution and primary amino acid sequence.

Thus, a protein index of interest is one wherein proteins are characterized by having at least three descriptive parameters thereof, pI, MW and tested for expression in a variety of tissues, at least five tissues having been examined for expression thereof, as provided hereinabove. Moreover, the tissues can be obtained from a single individual of a panmictic population to control polymorphism and normal variation.

Another way to index the proteins is to characterize each spatially in the context of a gel pattern. While molecular weight and pI are determinative of the location of a protein spot on a gel, the relationship of any one protein spot to another spot or other spots on a gel can provide additional identifying parameters of the proteins. Frequently, identical proteins behave slightly differently in different samples to give a slightly different gel location. In addition, some variance may be observed in different batches of gels being run.

By aligning two patterns in a best fit ("spatial matching" or "warping"), spots that are shared by two samples and spots that appear to be unique to one or the other, in the absence of specific sequence data, may be revealed. Such pair-wise comparisons can be made over any combination of samples. The warping process to obtain a best fit of patterns comprises not only a static matching of gel patterns but also an electronic manipulation of patterns by, for example, stretching, rotating, shrinking and so on portions of one or both gels being compared to maximize the register of spots or landmark spots on the gels.

A number of different measures, or combinations thereof, for determining distance or similarity of protein or of spots can be employed. For example, suitable measures of distance and/or similarity for use with cluster analysis, multiprototype classification and multidimensional scaling are Euclidean, average Euclidean, Mahalanobis, Minkowski, average Minkowski, maximum value, minimum value, absolute value, shape coefficient, cosine coefficient, Pearson correlation, rank correlation, Kendall's tau, Canberra, Bray-Curtis and Tanimoto, also known as Jaccard coefficient.

A comparing means is used to analyze spectra, or other identifying features, of the spots occurring on two or more 2-D gels. A similarity threshold may be selected to identify spots that could be the same. Alternatively, a more complex clustering threshold can be used. Denoted spots having similar spectra and that have similar positions (as judged by the X and Y positions of the spots on the 2-D gels after alignment by the imaging means) can be considered likely candidates for identity.

A large number of such pairs (in the case of a comparison of two gels) are analyzed by a comparing means as a group to yield a best fit and hence to derive a global geometrical mapping of a plurality of spots on a gel. That mapping to form a two dimensional spot pattern which then forms the basis for a generalized matching wherein newly obtained spots are compared to those spots that comprise the standard pattern of proteins that have been characterized and already exist in the index.

Judicious choice of very diverse and very similar tissues could reduce the number of pair-wise comparisons that might need to be made. Having a scanning means and data storage means also would minimize the number of actual comparisons that need be made as a computer processing means can make those comparisons.

Thus, such a spatial analysis provides additional identifying parameters of a polypeptide comprising an index of interest.

Assignment of spots that are matched to a particular locus, site, address or cell on the reference 2-D gel can be validated, for example, by employing techniques providing additional information, such as, fragment mass, detailed molecular weight information or sequence information as can be obtained, for example, using MS, LC/MS/MS or actual sequencing, of the proteins of interest. Other methods of determining identity of proteins between and among gels include binding by a specific ligand or co-factor, a receptor lectin or an antibody.

To obtain such additional information, a protein may be isolated from the 2-D gel matrix. A suitable technique is to isolate the individual protein spots and to extract and to purify the protein(s) from the matrix. That can be accomplished by known means and methods. A spot can be excised manually or robotically, based on scanning or previously obtained information contained in the index as to a protein's location in a warped 2-D gel, by means of a robotic spot cutter controlled by a-processing means.

Then, the purified preparation of a protein or proteins with a particular molecular weight and pI are analyzed by another method of characterization, such as, sequencing, immunologic identity, liquid chromatography or mass spectrometry (MS). There are methods of MS that are suitable for analysis of biomolecules, such as proteins. Some of those MS methods include matrix assisted laser desorption ionization (MALDI) MS, LC/MS/MS (liquid chromatography/tandem mass spectrometry) and MALDI-time of flight (TOF) MS. LC/MS/MS is particularly useful when analyzing hydrophobic proteins, such as membrane proteins, and for providing primary amino acid sequence data.

To conduct MALDI MS or MALDI-TOF MS, it may be necessary to take the proteins contained in a spot and to digest same to produce a collection of smaller oligopeptides as the smaller molecules are more amenable to separation and identification by those techniques. The means to obtain the oligopeptides are known and include mild hydrolysis by acid or base, digestion with particular proteases, peptidases, cyanogen bromide and so on. A number of oligopeptides from a single protein spot can be analyzed. A suitable size of the oligopeptides is on the order of about 5 amino acid residues to about 30 amino acid residues, however, those size limits are variable and can be dictated by the cleavage method and the level of discrimination afforded by any one particular analyzing means that is used. Thus, the mass spectrometry data provides information on the mass of peptide fragments of the polypeptide(s) comprising a spot.

MALDI MS data enables identification of the same protein on different 2-D gels. MALDI MS data can identify the parent protein in a sequence database search particularly when the oligopeptide is unique for the protein. Uniqueness is enhanced for proteins encoded by single copy genes or when the oligopeptide is larger.

LC/MS/MS provides additional information, particularly, actual amino acid content of a peptide. Each of the peptides is fragmented and the masses of the fragments are measured. In general, the peptides fragment at the peptide bonds. Thus, the fragments generated have masses differing by amino acid masses, which average about 100 daltons each. Therefore, by interpreting the fragment masses, it is possible to ascertain the amino acid sequence of the peptide. The result is a protein wherein the specific primary amino acid sequences of portions thereof are known.

The MS peak data (essentially a table of the masses of the peptides obtained from each spot) also can be compared by a data processing and comparing means to obtain relationships between and among spots. That data can be manipulated to obtain relative spot:spot similarities. That exercise can obviate the need for the actual sequence of certain peptides.

The use of mass spectrometry (MS) and other protein identification methods to provide additional information on each protein spot facilitates the comparing, matching and collating of 2-D gel patterns into a coherent, all encompassing reference protein database that accounts for normal variation, tissue-specific differences, cellular differences and so on.

To assist in determining identity of proteins, the 2-D gel patterns of proteins from different sources can be compared. Therefore, the patterns of two gels are compared to determine which protein spots are held in common between and/or amongst the gels. That exercise also will reveal which protein spots vary and in what manner those proteins vary. By varying the source of the proteins, such a comparison also will reveal what is normal variation of a protein and whether a protein is specific for, for example, an organelle, a cell or a tissue.

To minimize polymorphism, particularly in the case of a randomly breeding population, tissues from an individual could be used. Thus, samples are obtained from a single genotype therefore minimizing genetic variability imposed at the population level. Intraindividual variability should be revealed, such as between tissues or cells. Moreover, the information is obtained from primary tissues as compared to, for example, cell lines, which often are transformed in some fashion.

Another means for assisting in demonstrating similarity between two samples is to combine two protein sources to provide a mixture for separation in a gel. A gel containing the separated protein mixture is compared with the gel patterns of each protein source separated individually to obtain a spatial comparison. The mixtures can be at an even 1:1 ratio of the amounts of the two protein sources or can be in other predetermined ratios, for example, in a graded series of mixtures, such as, 1:10, 1:2, 1:1, 2:1, 10:1, wherein the ratios represent the relative amounts of the two parental protein sources. Other ratios can be used. The various samples are separated by 2-D gel electrophoresis. The 1:1 mixture reveals spots specific for one or the other protein source. Then by comparing the gels of the graded mixtures, the change of a spot based on protein source can be observed. That exercise allows an assessment of spot identity with two sources. If the spot relocates in the graded mixtures, it is likely two distinct nearby spots would be seen in the gel of the 1:1 mixture.

By combining 2-D gel electrophoresis with a further protein identification means, such as mass spectrometry, it is possible to identify spots as likely to be the same on different gels, and thus, for example, originating from different organs, tissues, cells, organelles and so on. There may be spatial dissimilarity of the spots between and/or among gels. That can arise, for example, by experimental sources or natural sources. Experimental sources can be identified and minimized by refining techniques, such as consistency of materials and methods. Other sources of variation may be inherent in the molecules, such as allelic variation and so. All such data are diagnostic.

Hence, the data will reveal the general location of a particular spot on a 2-D gel and therefore, spots can be aligned between and/or among gels despite variations in spot location on one or more gels.

Such identified spots can serve as landmarks for the warping procedure when comparing plural gels for a best fit. Warping can occur on 2-D gel patterns without further characterization of spots. However, further characterizing information lends confidence to the establishment of landmark spots. The further characterizing need not require total identity such as revealed by sequencing. Provisional identity can be obtained by immunological studies, other specific binding to cofactors, substrates, subunits, etc., partial sequencing, fragmenting the polypeptide and so on. For example, mass spectrometry, such as MALDI-TOF, would provide information on peptide fragment masses in a high throughput manner. The nature of fragmentation and the masses of the fragments can be diagnostic for a polypeptide residing in a spot.

By such identification, provisional or proven, of particular spots in various sites of a gel, the warping of gel images can be redone to account for a greater array of spots.

In addition, by such identification, it is possible to determine with confidence, without employing a particular protein identifying means, the identity of a spot on succeeding gels, if that spot localizes to an area where a known protein localizes. The accumulated data will provide a zone where an identified protein exists, even if that protein exhibits viability in different individuals, organs, tissues, cells and so on.

The value of such identification of particular spots on a gel, for example, by mass spectrometry, is that by selection of a subset of spots localized to various regions of a gel, only that subset need be identified to enable warping of gels to reveal spots of likely identity and those specific to a gel, and thus specific to the source of the proteins.

The identification of only a subset of landmark proteins or spots and warping enables a more rapid comparison of a plurality of gels and a provisional assignment of protein or spot identity in succeeding gels. Thus, a spot, not previously identified, that is found to reside at a particular location on a number of gels with or without warping, can be provisionally considered the same polypeptide or protein. That provisional assignment can be confirmed by a particular protein identification means, such as, an immunoassay or mass spectrometry.

In addition, by identifying certain landmarks and warping, there no longer is a need to compare 2-D gel spot patterns that appear grossly similar. If the landmarks represent proteins found in a wide range of sources, and either the protein shows little or no variation or a confident level of variation is known, then the gel pattern of any new source can be compared to the reference gel pattern.

The greater the number of landmarks, the more exacting the warping process may be. However, at the onset, comparisons can be made with as few as 5 landmark spots. Preferably, there are more than 5 landmarks and with each provisional or proven assignment of spot identity, the landmark data base is enhanced.

An outcome of the development of landmarks is a theoretical reference spot pattern containing the landmarks. Proteins of low variability will appear as discrete spots with sharp borders. Proteins more variable will be represented as a zone or region of location, the radius of the zone correlating to the amount of variability observed. That reference pattern may find use with the gel patterns of a wide range of protein sources.

Therefore, gels in which 90% or more of the spots are identical can be compared. But gels of lesser similarity can be compared by warping, such as gels with 80% or greater spot identity; gels with 70% or greater spot identity; gels with 60% or greater spot identity; gels with 50% or greater spot identity; gels with 40% or greater spot identity; gels with 30% or greater spot identity; or even gels which overtly appear dissimilar but for the landmark spots.

The spatial and additional spot characterization, such as MS data, enable relaxing the spatial stringency of the matching process by introducing additional identifying information for each peptide and each protein. The spatial and MS data also can reduce the number of tissue combinations that need to be performed to identify and to characterize a protein.

The storage means acquires the data so collected and catalogs said data in a storage means for later analysis. A collating and comparing means on an individual protein can determine, for example, whether a spot revealed by one staining procedure is the same as another spot revealed by another staining procedure. That type of comparative analysis also will reveal whether different staining procedures, different gels, different gel separation procedures and the like, result in variation in the location of a protein based on molecular weight and pI on the 2-D gel.

The comparing means of MS data and spot matching can involve the step of comparing all spectra against each other according to some particular distance metric to yield a matrix of the similarity of each spot to all the other spots. Alternatively, the comparing means may independently, or in conjunction with the above, cluster the spots that are similar to one another. Ideally, clusters contain the same protein even when expressed in different tissues.

A preferred means for comparing and analyzing the data in the development of a protein index is to have the data obtained, stored, processed, analyzed, compared and so on in a form and manner that is compatible with a computer. Thus, for example the data is archived in digitized form on a computer readable medium.

To know which protein spots are versions of other spots, even within the same tissue, MS, for example, can provide insight to that relationship by demonstrating that a series of several spots on a gel have the same peptide mass pattern.

Thus, the MS data (e.g., MALDI peptide masses) can be searched by a data comparing means to identify samples demonstrating similarity (of, for example, each spot of the gel to all other spots on the gel). The comparing means and data collation means will reveal clusters of spots that are likely (because of the similar peptides contained therein) to be versions of the same gene product.

Then each cluster is analyzed by a comparing means to select members having a very similar molecular weight, indicating that the selected proteins have the same or very similar polypeptide chain length and composition. The selected proteins then are analyzed further by a comparing means to determine if the pI separations between and among the proteins are consistent with differences amounting to integral charges, the most likely scenario if the proteins are simple chemical isoforms of one another.

The identification exercise can be facilitated if the protein is matched with a full-length gene sequence encoding the protein. The full-length gene sequence can be used to compute a theoretical pI of the deduced amino acid sequence and a delta pI/charge value for the deduced amino acid sequence. The position of the protein spots then can be compared to the theoretical pI to determine which, if any, is likely to correspond to the unmodified protein. The comparing means also can be used to compare the differences in the pI positions with the calculated delta pI/charge to determine whether the putative isoforms of the same molecular weight are likely to be single charge variants of one another, the most likely result in phosphorylated proteins.

Members of a cluster can be analyzed further by a comparing means using quantitative data from various experiments to determine if there is an inverse variability between spots, which could be observed if the isoforms were transformed from one form to another by a modification process, or if there is coordinate variability between spots, which would be likely if all forms were increased or decreased together.

If a cluster contains one or more spots at the expected full length sequence position, and one or a small number of lower MW spots, then a comparing means can take the pI and MW of the smaller spots and compare those with the pI and MW predicted for various subsections of the full length sequence to determine if a subsection would be predicted to have the observed pI and MW. If so, some deductions may be possible regarding the nature of the process that results in production of the shorter product, for example, if the postulated fragment arises from putative alternate splice sites, then message splicing events are likely to be the cause of the differences. Alternatively, if the fragment has ends that are the likely cut sites of a specific protease, the characteristics of the protease may be deduced.

One may use a variety of ways to list the proteins in an orderly manner. An arbitrary alphanumeric descriptor can be assigned to the individual proteins. Alternatively, the proteins can be sorted by an individual parameter or characteristic, such as cell source, chromosome source, function, tissue source, pI, molecular weight, map coordinate position, some other name, symbol or acronym established from another list and so on. An artisan can select the criterion or criteria for ordering and selecting the proteins for ready accessibility.

A more complete description or definition of a protein will, therefore, contain an increasing set of descriptors, such as, the molecular weight and pI data, as well as MS data and protein name, if known. A large number of distinguishing characteristics would enhance reference value of the database. However, there may be for any one protein, a minimal set of unique defining characteristics that will be diagnostic for identifying that protein. That is true particularly for a provision assignment of identity. Moreover, the identify of a polypeptide or spot is not necessary for entry of a protein into the database.

The index will serve as a reference resource providing identifying characteristics of the polypeptides so that any newly identified polypeptide can be compared to those already cataloged to determine either the identity of the newly identified polypeptide or the need to incorporate the newly identified polypeptide as a new entry of the index.

As discussed hereinabove, identified proteins will establish landmarks on 2-D gels that will enable warping and fitting of gels to correct for variation in the proteins and running conditions.

Therefore, in the context of spots on 2-D gels, there are a number of sets and subsets of protein spots depending on apparent identity between gels, based on, for example, pI, MW, tissue distribution, mass spectrometry data, primary sequence and so on.

A number of spots will be identical between the two gels. The identical proteins can be identified as comprising population or set W. A subset of proteins of set W will yield spots on the gels that overlap or appear to fall at the same site on the gels, once the gels are properly warped to ensure a best fit between the two gels. That subset of seemingly identical protein spots comprises a population or set X. A subset of proteins of set X of the two gels will have the same mass spectra. That subset can be identified as population or set Y. Finally, a subset of set Y comprises proteins that have identical spectra that match a theoretical spectra based on the primary amino acid sequence on the protein. Those proteins comprise population or set Z. The proteins of set Z are those actually identified and are likely candidates as landmarks on 2-D gels. Proteins of subsets Y and Z, and perhaps subset X, once tested for expression in a variety of tissues, as provided hereinabove, are cataloged in the database.

The process for assigning a protein or a spot to one or more of the above sets, and also to determine the correspondence of protein or spot between two gels may proceed along the following chain of events.

The spot patterns of the two gels are digitized by an image scanning means. The information collected includes, for example, the density, size and shape of the spot.

For spots that meet predefined criteria for characteristics of the spots, such as spot size, spot density, approximate pH, approximate molecular weight and so on, those spots are excised from the gel by a spot extracting means so as to isolate the protein or proteins that comprise the spots.

The gel matrix is treated to enable extraction of the polypeptide(s) contained therein. Known methods are practiced.

The samples comprising one or more polypeptides are treated, such as with an enzyme, for example, a protease, such as trypsin, practicing known methods, to digest the polypeptide(s) into smaller peptide fragments.

The polypeptide fragments then are analyzed by mass spectrometry, such as MALDI or MALDI-TOF MS to obtain mass spectra for the spot contents.

The mass spectrum of the individual spots is compared to that of known proteins provided in available databases using an algorithm such as MaldiMatch to organize data and to assign spots and proteins to population or set Z.

Then the data of the spots are compared between the two gels using an algorithm, such as MaldiMatch, at high stringency to identify proteins that comprise population or set Y. By high stringency is meant the parameters defining the search and analysis of data are configured to provide high sensitivity. For each spectrum, peaks are detected using known algorithms, such as RADARS, to yield a set of centroid m/z peaks that are reporting in Daltons and relative intensity. Then the comparing algorithm, such as MaldiMatch, performs a dynamic calibration that entails rounding the molecular weight assignments for 10–20 of the most intense peaks of a spectrum to the nearest 1–2 Dalton units. Pairs of peaks of similar molecular weight are identified and the difference in high resolution mass is calculated. If a significant number of pairs are identified, a search is conducted to determine if a common mass difference or a mass difference or offset that affects all or a significant number of pairs of peaks is present. Then, one or both of the spectra are modified by adjusting the peaks therein by the calculated offset or molecular weight difference. Then, the spectra similarity is calculated where the similarity is a function of all mass peaks and the intensity thereof in either spectrum. Similarity values above an empirically derived threshold are considered matches. The threshold is one that is derived by conducting the above exercise for known proteins.

The data of set Y are used as initial landmarks in an algorithm, such as Kepler, that conducts the initial image processing and analysis, the proteins of set Y comprise the landmarks to facilitate the warping of gel images to bring remaining spots into alignment in a best-fit accommodation.

Those spots of both gels not yet assigned to set Y that have similar positions following warping are tentatively assigned to population or set X.

Each pair of associated spots from the two gels is analyzed by mass spectrometry and spectrum matching as described hereinabove to confirm the tentative identity of the spots and the protein contained therein. The spectrum-matching algorithm, such as MaldiMatch, will be run at high specificity. Peaks are detected and reported in Daltons. Peak intensity also is recorded. That data comprises the peak list. All peaks are rounded to the nearest 1–2 Daltons to overcome calibration-related differences between identical samples. For each spot of one gel, the peak list thereof is compared to all peak lists for spots on the other gel. For a given comparison of peak lists, similarity is measured as function of all the peaks present in both lists, as well as the intensity thereof. An empirically derived threshold is used to select candidate matches. The threshold is derived by comparing known proteins. Candidate matches are subjected to dynamic post acquisition calibration and the similarity is recalculated. An empirically derived cutoff is used to determine if the spots in question have the same protein constituents. The cutoff is derived from studies done with known proteins. That analysis detects true differences between spots and yields proteins or spots that comprise population X.

The data of proteins comprising population X then serve as landmarks in another iteration of the image analysis to again warp the gels. Spots on the gels found at the same position in the warped gels but not already assigned to set X are tentatively assigned to set W.

To confirm assignment of the proteins to the various sets, individual proteins can be further examined, such as by LC/MS/MS to determine primary amino acid sequence for comparison, if available, to known sequences of known proteins.

In the above described spectrometry data comparison analysis, a variety of matching algorithms, such as Jaccard coefficient or weighted Jaccard coefficient, can be used. In the Jaccard coefficient, data is transformed by obtaining the ratio of the number of peaks appearing in both spectra divided by the number of peaks appearing in one or more spectra.

When the data collation and comparisons are completed, the characterizing information for each polypeptide then is stored. The method of storage is variable and sorting can be based on any of a variety of the characteristics of the polypeptides. The database can contain entries for at least 10 polypeptides; at least 15; at least 20; at least 25; at least 30; at least 40; at least 50; at least 60; at least 70; at least 80; at least 90; at least 100 proteins. A database of interest is one wherein each of the polypeptides therein has been tested for expression in plural tissues as provided hereinabove. Thus, for example, each of 10 proteins has been tested for expression in at least 5; at least 6; at least 7; at least 8; at least 9; at least 10; at least 11; at least 12; at least 13; at least 14; at least 15; at least 16; at least 17; at least 18; at least 19; or at least 20 tissues. More than 20 tissues can be examined.

As discussed hereinabove, a suitable first step is to develop a database that accounts for the proteins of a number of different tissues. Preferably, the tissues are obtained from members of an inbred strain or an individual to minimize variation. The inbred strain can be of a microbe, plant or animal. The microbe, plant or animal can be wild, of agricultural significance (whether desired or pests) or for laboratory use. Suitable examples are agricultural livestock and crops, laboratory animals and so on. The database can include cellular and subcellular information. Populational variation can be quantified by studying samples from plural individuals of a population. It may be possible to make interspecies comparisons with samples obtained from the same tissue but from different species.

The index can provide a variety of uses beyond the identifying purposes. For example, the index can be used to reveal metabolic changes of an organelle, cell, tissue and so on under varying environmental conditions, such as, for example, temperature change, exposure to a typical states and environments, chemicals and so forth. For example, exposure to a particular biological inducer can result in expression of previously under expressed or unexpressed proteins, loss of or lowered expression of certain proteins and variation in certain proteins. Other conditions include exposure to toxins or to pathogens. In addition, changes in protein expression can arise from a disease state or as a natural result of aging.

Finding proteins that arise in a disease state will enable the development of diagnostic assays, which may be 2-D gel electrophoresis together with other associated methodologies, such as mass spectrometry, but could also be other diagnostic means, such as a nucleic acid-based assay or an immunology-based assay, such as an ELISA, once a particular diagnostic protein is revealed.

Another source of proteins for study are cell lines that can be maintained in vitro for long periods of time. The protein index may provide a basis for selecting certain cell lines as being particularly, if not wholly, representative of a naturally occurring cell, tissue, organ or organism.

In a similar vein, the proteins of a biopsy specimen or primary cell, tissue or organ culture can be studied to monitor the status of the cells across multiple passages to ensure the culture remains useful for the intended purpose.

As discussed hereinabove, when spots and/or proteins diagnostic for the source of protein are identified, the actual diagnostic assay need not be 2-D gel electrophoresis or mass spectrometry, but can be any assay specific for that diagnostic protein, such as specific binding assays, such as an ELISA.

At some point in time, the need for the initial protein characterization by, for example, 2-D gel electrophoresis, may be unnecessary and other methods may be employed to provide sufficient diagnostic information to provide a provisional, if not exact, identification of a protein.

For example, a particular protein may be available in pure form. That protein can be fragmented and the fragments examined by mass spectrometry to yield fragmentation pattern and fragment mass. That information may be diagnostic, thereby foregoing the need for 2-D gel electrophoresis. Such a 2-D gel bypass is not reliant solely on mass spectrometry, such as MALDI-TOF that is high throughput, but can be any method that reveals diagnostic information on the protein, and that diagnostic information exists in the database.

The database of interest permits new analytical measurements other than the conventional "control vs. treated" experiment structures. The instant invention is directed at the analysis of multi-experiment databases. The methods provide better tests of the significance of observed changes, and allow the comparison of one set of changes with another for purposes of mechanism classification. Results of such a large-scale analysis of the effects of 50 different drugs has been done, including the identification of protein markers for efficacy and toxicity.

A second area of interest is in the comparison of various human tissue proteomes. The tissue-to-tissue similarities and differences observed in the practice of the instant invention provide insights into the relationship between structure and function at the organismal level, as well as in the process of development.

By measuring the abundance of every or at least a very large number of proteins in a particular tissue, cell type or fraction from a statistically significant number of individuals, one can prepare a distribution of amounts for each protein. Using statistical analysis, such as 2 or 3 standard deviations, one can state that certain proteins are higher or lower in abundance in certain individuals. If those individuals are unique in any manner, such as having a disease, one may suspect the protein(s) are markers for the disease and perhaps are involved in the disease mechanism in some fashion. The association-based hypothesis is then provable by later experiments.

By observing when certain combinations of proteins appear simultaneously or antagonistically, such the when the expression or appearance of one can predict the expression or appearance of one or more other proteins, the expression of the two or more proteins may be correlated, either positively or negatively. That implies that the genetic control of those proteins may be co-regulated in some manner. It is also likely that some combinations of co-regulated proteins represent at least part of a metabolic pathway.

For example, 80 pairs of monozygotic twins were selected for maximal disease phenotype discordance. The within-pair differences are indicative of pure non-genetic disease phenotype effects. That was done to reduce background noise due to polymorphisms. Within-pair correlations were made.

Figure 3:
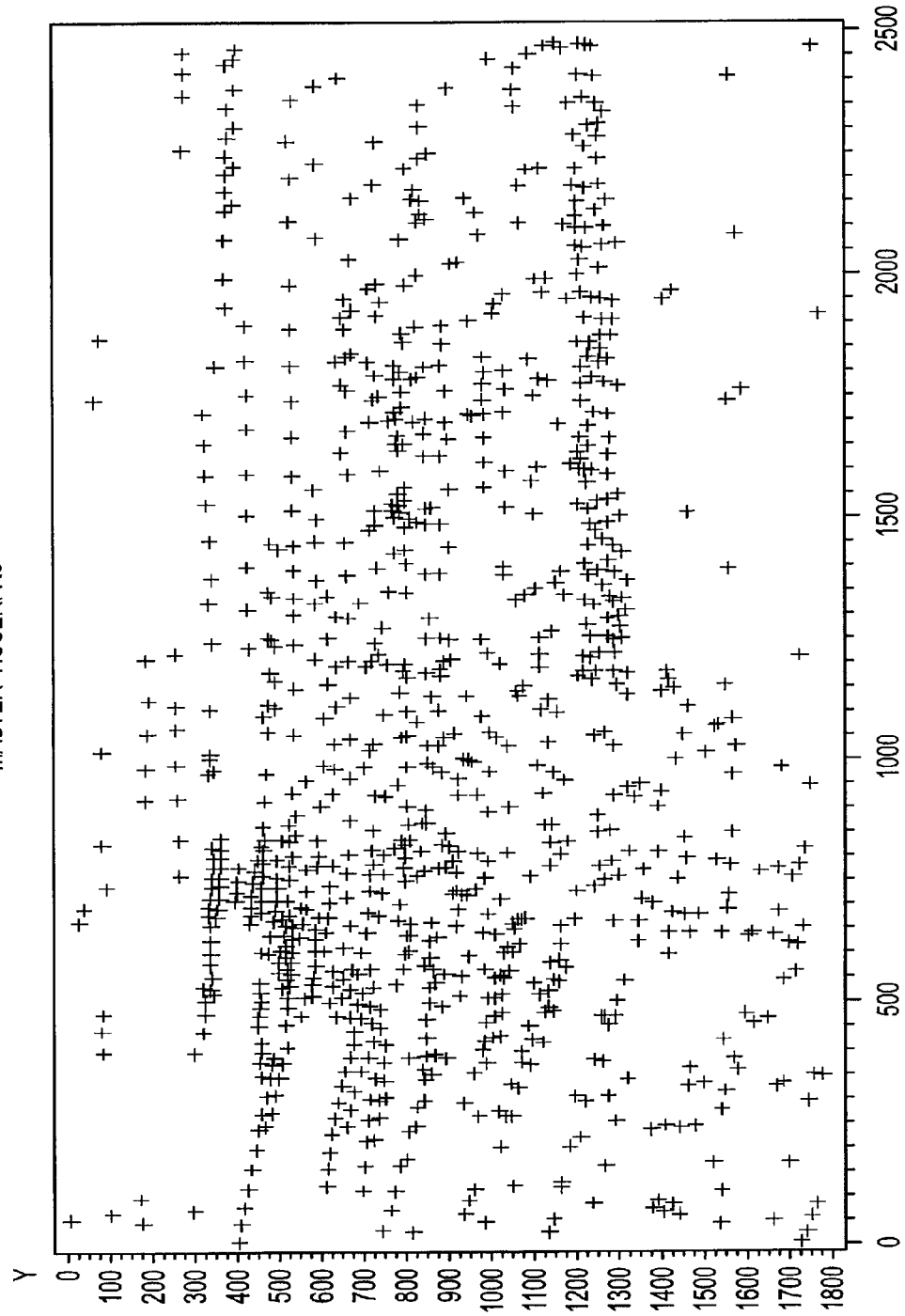
FIG. 3 is a pixel display of spots from a two dimensional gel (2DG) from 160 individuals of serum proteins with common serum proteins immunosubtracted. The x coordinate is a digitized measure of protein isoelectric focusing points and the y coordinate is a digitized measure of the molecular weights such that the graph resembles the conventional format for displaying two-dimensional gels
Figure 4:
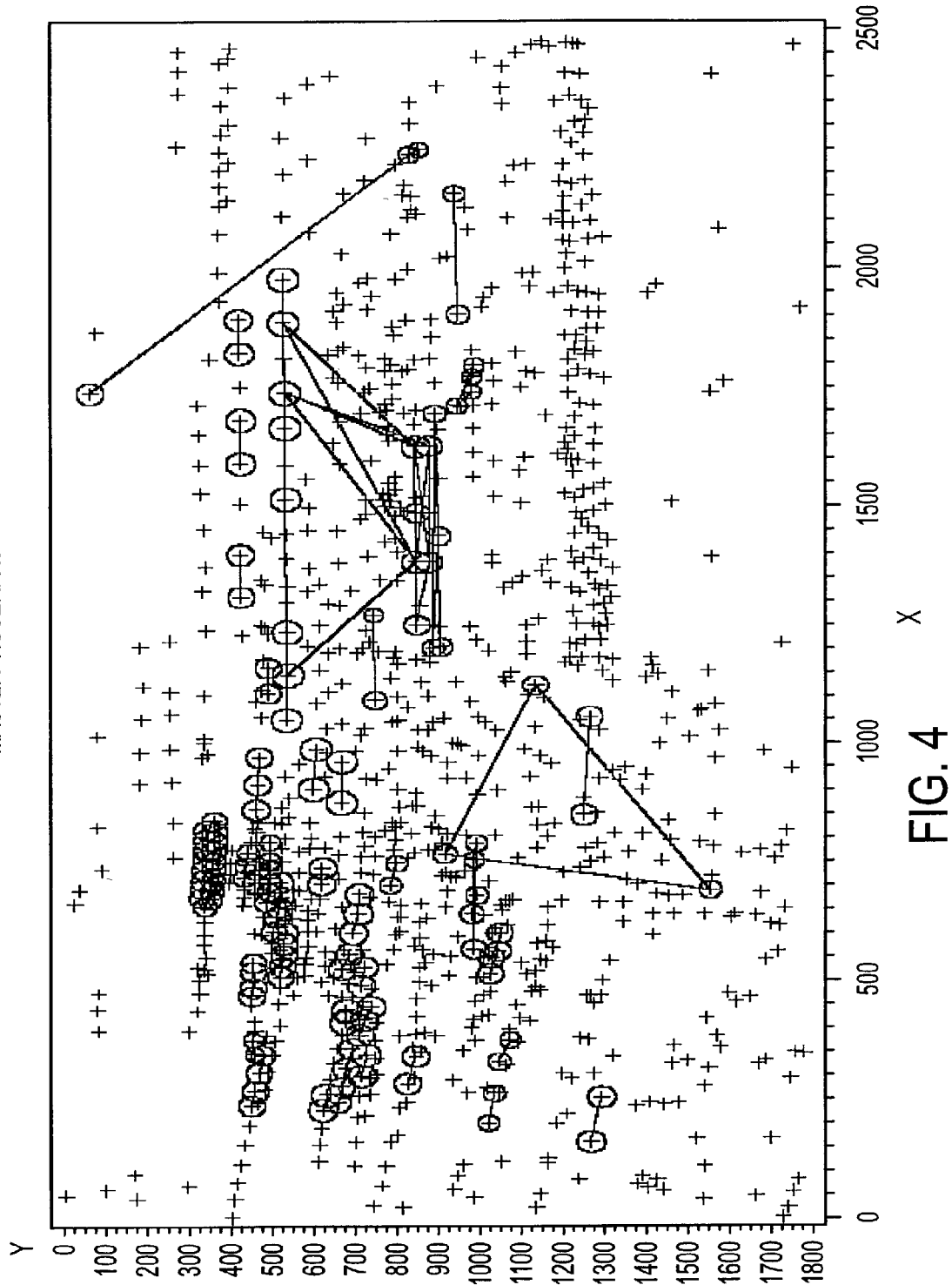
FIG. 4 is the same display as FIG. 3 with co-regulating proteins being represented by circled spot areas and the corresponding near-perfect correlations indicating coregulated protein connected by a line. At least some of the horizontal lines are believed to represent the same protein with a different glycosylated form resulting in a slight charge shift with minimal molecular weight change.
Figure 5:
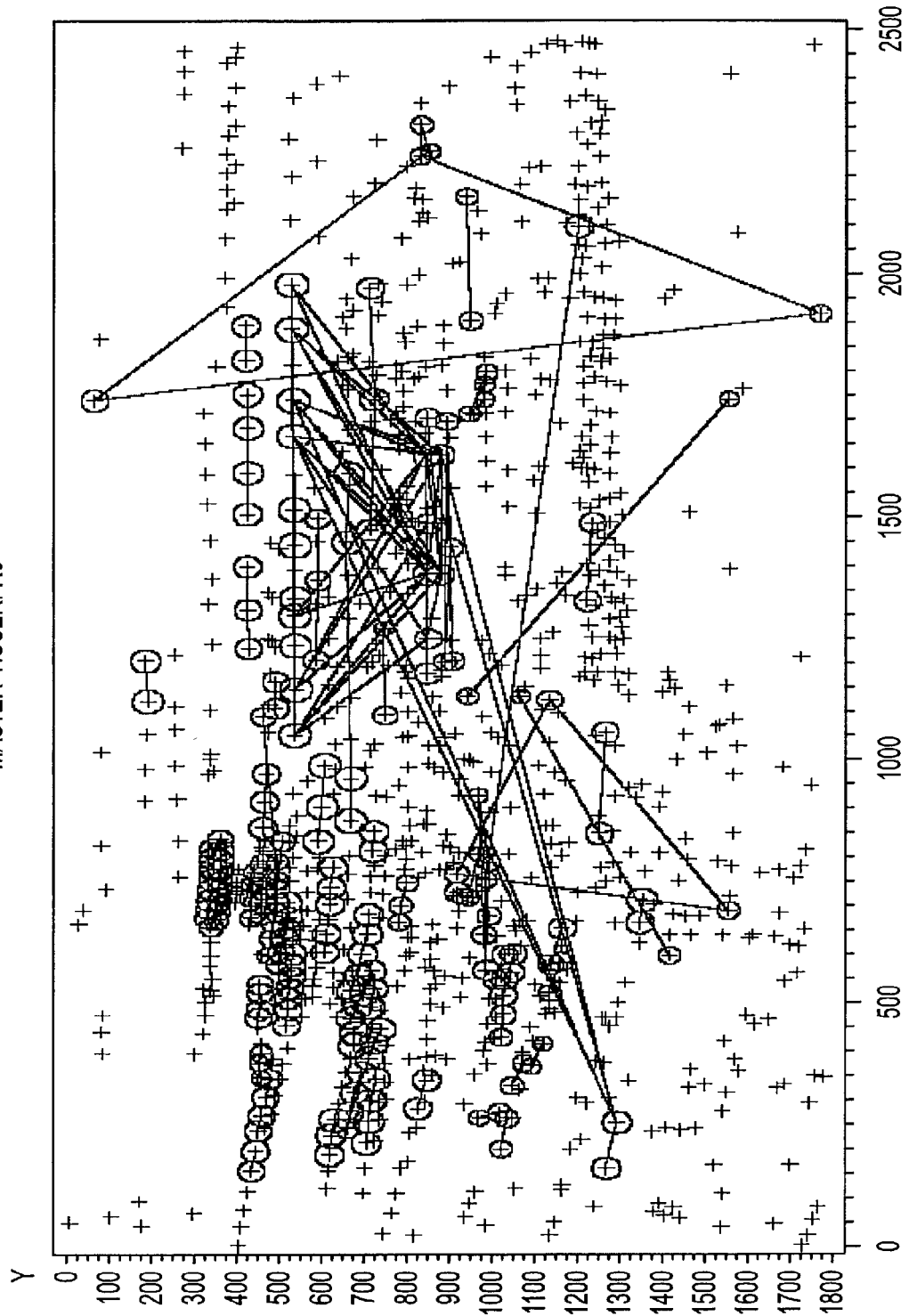
FIG. 5 is the same as the display of FIG. 4 showing very strong correlations.
Figure 6:
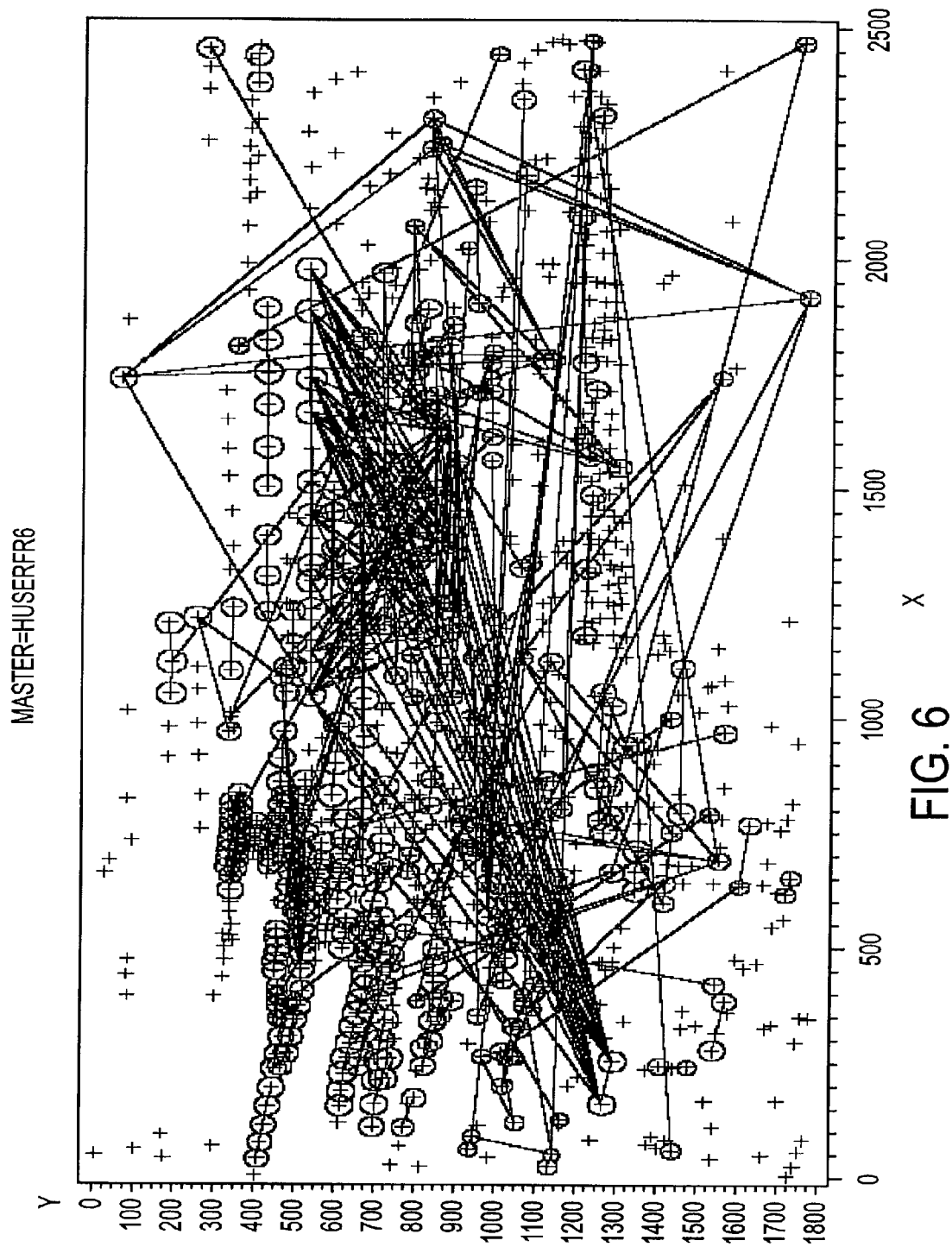
FIG. 6 is the same as the display of FIG. 5 where all statistically significant correlations are depicted.

A master spot pattern of 970 spots was generated for 32 twin pairs, see FIG. 3. Spot to spot correlations across the subjects was performed to detect apparently co-regulated proteins. A 118 spot subpattern classified 64 subjects into pairs with 88% accuracy. The results are given in FIGS. 4–6 with lines between spots indicating proteins that appear to be co-regulated by virtue of a correlated pattern of expression. The number of correlations suggests that metabolism is considerably more complex that previously thought.

A complete Human Protein Index (HPI) would mark the completion of human protein molecular anatomy, with each protein described, all stages in the maturation and transport thereof described, and the mature place of the protein in cellular molecular anatomy known. Fortunately, the same technologies and processes required for the HPI are those required to explore development, cell function and disease states at the molecular level.

One of the most basic questions in biology concerns the mechanisms and program underlying differentiation. Differentiation can be viewed as a progressive diminution of gene expression in a cell as various genetic programs are relegated to non-expression. Metaplasia, dedifferentiation and redifferentiation are other manifestations of the basis theme, albeit at lesser occurrence. In those circumstances, the exception occurs and quiescent genetic programs are once again active or may never have been silenced.

Many theoretical approaches have been formulated to describe how differentiation operates. Those almost invariably postulate the existence of sets of batteries of genes that are switched on or off together, and that are organized to be expressed in a prearranged sequence. In the simplest case, one set of protein gene products would contain a derepressor activating a second set, while the second set would contain a repressor for the first and a derepressor for a third. Such a chain of events could be irreversible.

While many examples of coregulation of gene expression are known, no protein database or index contains definitive examples. Further there is disagreement as to whether the organization of the genome operating system is such that relatively few co-regulated sets exist, or whether, as has been proposed, all proteins are part of an interconnected signaling network in which the presence, absence, or change in abundance of any one protein causes changes in the abundance of many others.

Many of those questions can be approached by selectively analyzing the data obtained in the practice of the instant invention. One can sort the data to reveal proteins are found in all nucleated somatic human cell types, and hence may be assumed to be part the general housekeeping systems. Others may be unique to a stage in the cell cycle, to one or a few cell types, to certain stages in differentiation, or to cells derived from one germ layer. The problem of coregulated sets may be approached by asking which proteins are always either expressed together, i.e., if one, then all, if not one, then not all.

Some genes may not be switched off at any time and may be part of a basic housekeeping set. Computerized searching of the data contained in the HPI allows both candidate co-regulated sets and the set of basic housekeeping proteins to be identified. Confirmation of a set identification may be made by using inhibitors that up or down regulate one member of a putative set, to see if other presumed members are similarly affected.

Instances are known where introduction of an inhibitor of one member of a co-regulated set produces up regulation of that member, a concomitant decrease in the biochemical activity of the factor, and coordinated up regulation of another member of the set. That mechanism, termed a "carom shot", is the only currently known technique for up regulating expression of a particular gene. Hence, the identification of members of coregulated sets is of great pharmacological significance.

Since many proteins have diagnostic significance, there is also a need for detecting and quantitating defined sets of proteins in body fluids and tissue samples, using simple and ultimately inexpensive methods analogous to DNA chips. Protein chips that carry a wide array of distinct proteins can be made and used to screening and diagnostic purposes, see for example, U.S. Ser. Nos. 482,460 and 628,339.

All references cited herein are herein incorporated by reference in entirety.

It will be evident to the artisan that various changes and modifications can be made to the teachings herein without departing from the spirit and scope of the invention of interest.

We claim:

1. A method for processing data in a database contained in a storage medium, comprising the steps of:
   (a) storing in the database, data that includes at least one pattern of a plurality of molecules found in a sample containing a plurality of molecules, the data based upon a statistically significant number of different samples, the data including at least one parameter, which is data output from a mass spectrometry analysis, for each of the molecules found in each sample;
   (b) comparing unknown data that comprises at least one parameter, which is data output from a mass spectrometry analysis, for each molecule found in a test sample with the data stored in the database;
   (c) recording differences and similarities between the unknown data and data stored in the database;
   (d) classifying a state of a sample by the steps of:
      1) detecting a test pattern in the unknown data;
      2) comparing the test pattern in the unknown data with the stored patterns in the database to identify differences and similarities; and
      3) using the identified differences and similarities to confirm the state thereof.

2. The method of claim 1, wherein the at least one pattern represents multiple proteins or polypeptides found in a single sample.

3. The method of claim 1, wherein the parameter is molecular weight.

4. The method of claim 1, wherein the samples are selected from the group consisting of serum, organ, tissues, cells, organdies and fractions.

5. The method of claim 1, wherein the differences and similarities in the database indicate one of the following states: aging, disease, presence of a toxin and presence of a pathogen.

6. The method of claim 1, wherein the state is selected from the group consisting of: a disease state, the presence of a toxin, the presence of a pathogen and aging.

7. The method of claim 1, wherein the pattern is a discriminatory pattern.

8. A computer program embedded on a computer readable medium storing a program for performing the steps comprising:
   (a) storing in the database, data that includes at least one pattern of a plurality of molecules found in a sample containing a plurality of molecules, the data based upon a statistically significant number of different samples, the data including at least one parameter, which is data output from a mass spectrometry analysis, for each of the molecules found in each sample;
   (b) comparing unknown data that comprises at least one parameter, which is data output from a mass spectrometry analysis, for each molecule found in a test sample with the data stored in the database;
   (c) recording differences and similarities between the unknown data and data stored in the database;
   (d) classifying a state of a sample by the steps of:
      1) detecting a test pattern in the unknown data;
      2) comparing the test pattern in the unknown data with the stored patterns in the database to identify differences and similarities; and
      using the identified differences and similarities to confirm the state thereof.

9. The computer program of claim 8, wherein the data includes or indicates the molecular weights of the proteins or polypeptides in the patterns.

10. The computer program of claim 8, wherein the sample is selected from the group consisting of blood, urine, feces, saliva, sputum, tears, sweat, cerebral spinal fluid, pleural fluid, serums organ, tissue, cell, organelle and fractions thereof.

11. The computer program of claim 8, wherein the state is selected from the group consisting of: a disease state, the presence of a toxin, the presence of a pathogen and aging.

12. The computer program of claim 8, wherein the pattern is a discriminatory pattern.

13. A method for processing data in a database contained in a storage medium, comprising the steps of:
   i) storing a pattern in the database, based on data, which is output from mass spectrometry analysis, that includes at least one pattern, a) said pattern being the presence of and abundance of a plurality of molecules and at least one parameter for each of said plurality of molecule, b) said pattern being found in a sample that contains the plurality of molecules, c) the data being based upon a statistically significant number of different samples previously analyzed wherein each different sample corresponds to a particular reference state, and d) the data including at least one parameter for each of the molecules found in each sample;
   ii) comparing unknown data from an output from mass spectrometry analysis that comprises the presence and abundance and at least one parameter for each of a plurality of molecules found in a test sample, with the data stored in the database by determining a test pattern in the unknown data that corresponds to plural molecules in a test sample;
   iii) classifying a state of a test sample by the steps of: detecting a test pattern in the unknown data; comparing the test pattern in the unknown data with the stored patterns in the database to identify differences and similarities; and using the identified differences and similarities to confirm the state of the test sample, and;
   iv) reporting the state of the test sample.

14. The method of claim 13, wherein the parameter is molecular weight.

15. The method of claim 13, wherein the samples are selected from the group consisting of serum, organ, tissues, cells, organelles and fractions.

16. The method of claim 13, wherein the differences and similarities in the database indicate one of the following states: aging, disease, presence of a toxin and presence of a pathogen.

17. The method of claim 13, wherein the state is selected from the group consisting of: a disease state, the presence of a toxin, the presence of a pathogen and aging.

18. The method of claim 13, wherein the pattern is a discriminatory pattern.

* * * * *